United States Patent [19]

Breuer et al.

[11] 4,128,723
[45] Dec. 5, 1978

[54] CYANOALKYLUREIDO CEPHALOSPORINS

[75] Inventors: Hermann Breuer; Uwe D. Treuner, both of Regensburg, Germany

[73] Assignee: E. R. Squibb & Sons, Inc., Princeton, N.J.

[21] Appl. No.: 883,602

[22] Filed: Mar. 6, 1978

Related U.S. Application Data

[60] Division of Ser. No. 765,037, Feb. 2, 1977, Pat. No. 4,096,329, which is a continuation-in-part of Ser. No. 664,128, Mar. 5, 1976, abandoned.

[51] Int. Cl.² .................. C07D 501/36; C07D 501/32; C07D 501/46
[52] U.S. Cl. ........................................ 544/25; 544/21; 544/28
[58] Field of Search ...................... 544/28, 25, 21

[56] References Cited
U.S. PATENT DOCUMENTS

| 3,996,217 | 12/1976 | Breuer et al. | 544/26 |
| 3,997,533 | 12/1976 | Kabbe et al. | 544/30 |

Primary Examiner—Paul M. Coughlan, Jr.
Assistant Examiner—David E. Wheeler
Attorney, Agent, or Firm—Lawrence S. Levinson; Merle J. Smith; Stephen B. Davis

[57] ABSTRACT

Cyanoalkylureido cephalosporins of the formula wherein R is hydrogen, lower alkyl, phenyl-lower alkyl, diphenyl-lower alkyl, tri(lower alkyl)silyl, trihaloethyl, a salt forming ion, or the group $$-\overset{R_5}{\underset{|}{CH}}-O-\overset{O}{\underset{\|}{C}}-R_6;$$

$R_1$ is hydrogen or methoxy; A is straight or branched chain alkylene or $$-\overset{}{\underset{R_2}{\overset{|}{CH}}}-;$$

$R_2$ is phenyl, 2-thienyl, or 3-thienyl; $R_3$ is hydrogen or lower alkyl; $R_4$ is hydrogen, lower alkyl, cycloalkyl, cycloalkenyl, cycloalkadienyl, phenyl, phenyl-lower alkyl, substituted phenyl, substituted phenyl-lower alkyl, or certain heterocyclic groups; $R_5$ is hydrogen or lower alkyl; $R_6$ is lower alkyl; and X is hydrogen, lower alkanoyloxy, or certain heterothio groups; are disclosed. These compounds are useful as antibacterial agents.

9 Claims, No Drawings

CYANOALKYLUREIDO CEPHALOSPORINS

This application is a Division of Ser. No. 765,037 filed Feb. 2, 1977 now U.S. Pat. No. 4,096,329 which was a continuation-in-part of Ser. NO. 664,128 filed Mar. 5, 1976, now abandoned.

BACKGROUND OF THE INVENTION

Cephalosporins having a ureido acyl side chain are disclosed in U.S. Pat. Nos. 3,673,183; 3,708,479; 3,833,568; and 3,860,591 and those also having a 7α-methoxy substituent are disclosed in U.S. Pat. Nos. 3,978,051; 3,989,693; and 3,989,697. Cephalosporins having various acyl side chains and a 7α-methoxy substituent are taught in various U.S. patents including 3,775,410; 3,780,031; 3,780,033; 3,780,034; 3,780,037; 3,843,641; etc.

Cephalosporins having an acylureido acyl side chain are disclosed in U.S. Pat. Nos. 3,687,641; 3,687,949; 3,925,368; 3,956,292; 3,954,802; and German Offenlegungsschrift No. 2,514,019.

SUMMARY OF THE INVENTION

This invention relates to new cyanoalkylureido-7α-methoxy or desmethoxy cephalosporin derivatives of the formula $$R_4-\overset{H}{\underset{\underset{R_3}{\overset{|}{N-A-CN}}}{\overset{|}{\underset{|}{C}}}}-\overset{O}{\overset{||}{C}}-N-\overset{R_1}{\underset{|}{\equiv}}\cdots \text{(cephem)}-CH_2-X \quad (I)$$

R represents hydrogen, lower alkyl, phenyl-lower alkyl, diphenyl-lower alkyl, tri(lower alkyl)silyl, trihaloethyl, a salt forming ion, or the group $$-\overset{R_5}{\underset{|}{CH}}-O-\overset{O}{\overset{||}{C}}-R_6$$

wherein $R_5$ is hydrogen or lower alkyl and $R_6$ is lower alkyl.

$R_1$ represents hydrogen or methoxy. The $R_1$ substituent is in the α-configuration as indicated by the broken lines (≡).

A represents straight or branched chain alkylene of 1 to 8 carbons or $$-\underset{\underset{R_2}{|}}{CH}-$$

$R_2$ represents phenyl, 2-thienyl or 3-thienyl.
$R_3$ represents hydrogen or lower alkyl.
$R_4$ represents hydrogen, lower alkyl, cycloalkyl, cycloalkenyl, cycloalkadienyl, phenyl, phenyl-lower alkyl, substituted phenyl, substituted phenyl-lower alkyl, or certain heterocyclic groups.

X represents hydrogen, lower alkanoyloxy, certain heterothio groups, $$-N\overset{\frown}{\bigcirc}, \text{ or } -N\overset{\frown}{\bigcirc}\overset{O}{\overset{||}{C}}-NH_2.$$

When X is pyridinium or carbamoyl substituted pyridinium, the compounds can be structurally represented as having the formula $$R_4-\overset{H}{\underset{\underset{R_3}{\overset{|}{N-A-CN}}}{\overset{|}{\underset{|}{C}}}}-\overset{O}{\overset{||}{C}}-N-\overset{R_1}{\underset{|}{\equiv}}\cdots \text{(cephem)}-CH_2-\overset{\oplus}{N}\overset{\frown}{\bigcirc}Z \quad (Ia)$$

wherein Z is hydrogen or carbamoyl.

DETAILED DESCRIPTION OF THE INVENTION

The various groups represented by the symbols have the meaning defined below and these definitions are retained throughout this specification.

The lower alkyl groups referred to throughout this specification include straight or branched chain hydrocarbon groups containing 1 to 8 carbon atoms, preferably 1 to 4 carbons. Examples of the type of groups contemplated are methyl, ethyl, propyl, isopropyl, butyl, t-butyl, etc. The lower alkoxy groups include such lower alkyl groups attached to an oxygen, e.g., methoxy, ethoxy, propoxy, etc. The phenyl-lower alkyl and diphenyl-lower alkyl groups include such lower alkyl groups attached to a phenyl, preferably benzyl, phenethyl, and diphenylmethyl.

The straight or branched chain alkylene groups referred to contain 1 to 8 carbon atoms, e.g., $-(CH_2)_n-$ wherein n is 1 to 8, $$-\underset{\underset{CH_3}{|}}{CH}-CH_2, -\overset{CH_3}{\underset{\underset{CH_3}{|}}{\overset{|}{C}}}-, -\underset{\underset{CH_3}{|}}{CH}-CH_2-\underset{\underset{CH_3}{|}}{CH}-, \text{ etc.}$$

Cycloalkyl refers to groups having 3 to 7 carbons in the ring, ie. cyclopropyl, cyclobutyl, cyclopentyl, cyclohexyl, and cycloheptyl. The term cycloalkenyl represent rings having 3 to 7 carbons with one double bond, i.e. cyclobutenyl, cyclopentenyl, cyclohexenyl, etc. The term cycloalkadienyl represents a ring having 6 or 7 carbons with two double bonds located at various positions such as 1,4-cyclohexadienyl which is preferred.

The substituted phenyl and substituted phenyl-lower alkyl groups include one or two substituents selected from halogen (preferably chlorine or bromine), lower alkyl of 1 to 4 carbons (preferably methyl or ethyl), lower alkoxy of 1 to 4 carbons (preferably methoxy or ethoxy), and hydroxy, e.g. 2-, 3-, or 4-chlorophenyl, 2-, 3-, or 4-bromobenzyl, 2-, 3-, or 4-hydroxyphenyl, 3,5-dichlorophenyl, 2-, 3-, or 4-methylphenyl,2-,3-, or 4-ethoxyphenyl, etc.

The salt forming ions represented by R may be metal ions, e.g., aluminum, alkali metal ions such as sodium or potassium, alkaline earth metal ions such as calcium or magnesium, or an amine salt ion, of which a number are known for this purpose, for example, phenyl-lower alkylamines such as dibenzylamine, N,N-dibenzylethylenediamine, lower alkylamines such as methylamine, triethylamine, and N-lower alkylpiperidines such as N-ethylpiperidine. Sodium and potassium are the preferred salt forming ions.

The halogens are the four common halogens, of which chlorine and bromine are preferred. In the case of the trihaloethyl group represented by R, 2,2,2-trichloroethyl is preferred.

Trimethylsilyl is the preferred tri(lower alkyl)silyl group.

The heterocyclic groups represented by $R_4$ are 2-thienyl, 3-thienyl, 2-furyl, 3-furyl, 2-pyridyl, 3-pyridyl, or 4-pyridyl. Also included within the meaning of $R_4$ are such heterocyclics having a halogen (preferably Cl or Br) or a lower alkyl of 1 to 4 carbons (preferably methyl or ethyl) substituent, i.e. 2-(4-chlorothienyl), 3-(4-methylthienyl), etc.

Lower alkanoyloxy refers to a group of the formula

wherein lower alkyl is of 1 to 4 carbons, preferably wherein lower alkyl is methyl.

The heterothio groups represented by X are

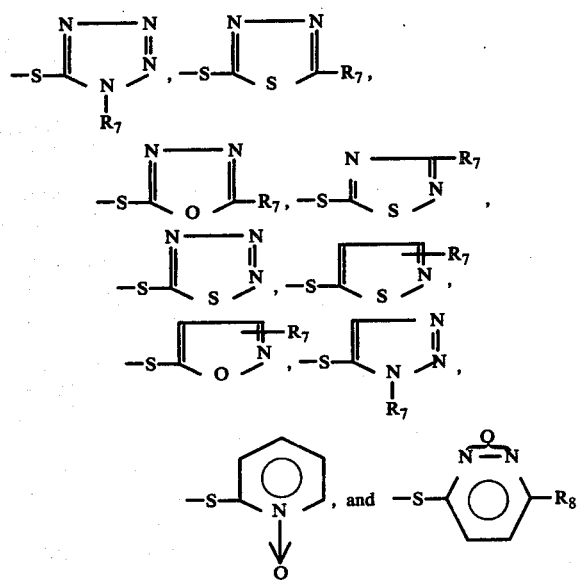

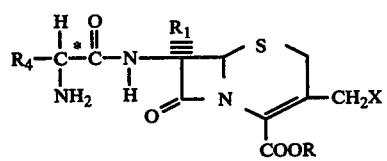

wherein $R_7$ is hydrogen or lower alkyl of 1 to 4 carbons (preferably methyl or ethyl) and $R_8$ is hydrogen, lower alkyl of 1 to 4 carbons (preferably methyl or ethyl), methoxy, hydroxy, or halogen (preferably chlorine).

The compounds of formula I can be prepared by several methods. For example, an α-amino compound of the formula wherein X is hydrogen, lower alkanoyloxy, or heterothio can be reacted, preferably in the form of its trifluoroacetic acid salt, with a compound of the formula

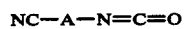 (III)

or

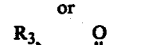 (IV)

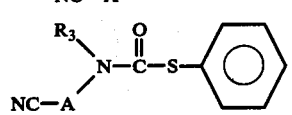 (V)

wherein A and $R_3$ are as defined above and halo is Cl or Br to yield the compound of formula I wherein $R_1$ is hydrogen or methoxy and X is hydrogen, lower alkanoyloxy, or heterothio.

The α-amino intermediate of formula II can be prepared by various methods such as by acylating a 7-amino cephalosporin of the formula

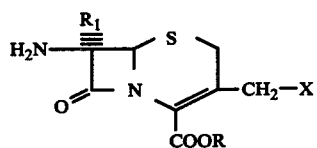 (VI)

with a substituted α-amino acid of the formula

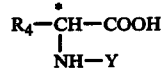 (VII)

wherein Y is a protecting group such as

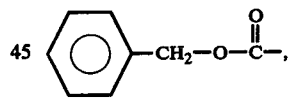

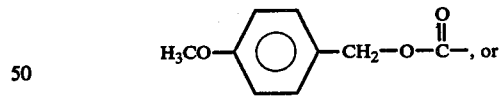 or

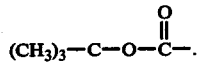

The α-amino protecting group is then removed by treating the resulting cephalosporin with trifluoroacetic acid and anisole. The α-amino compounds of formula II are taught in various U.S. patents as for example, Nos. 3,485,819; 3,507,861; 3,641,021; 3,796,801; 3,813,388; 3,821,207; 3,989,693; 3,989,697; etc.

The compounds of formula I wherein X is hydrogen, lower alkanoyloxy, or heterothio can be prepared by acylating a 7β-amino compound of formula VI preferably where R is an ester such as diphenylmethyl or trimethylsilyl with a compound of the formula $$\begin{array}{c} \text{H} \quad \text{O} \\ | \ast \ \| \\ R_4-\text{C}-\text{C}-\text{OH} \\ | \\ \text{NH} \\ | \\ \text{C}=\text{O} \\ | \\ \text{N}-\text{A}-\text{CN} \\ | \\ R_3 \end{array} \quad \text{(VIII)}$$

The carboxylic acid of formula VIII is perferably converted to an activated form such as an ester, mixed anhydride, or acid chloride derivative, or it can be reacted with thionyl chloride to yield an activated intermediate. Optionally, the acylation reaction is performed in the presence of a coupling agent such as dicyclohexylcarbodiimide. The resulting ester product is then treated according to known methods to remove the ester group and yield the compounds of formula I wherein R is hydrogen.

The intermediates of formula VIII can be prepared by reacting an isocyanatoacetic acid ester of the formula $$\begin{array}{c} \text{H} \quad \text{O} \\ | \ast \ \| \\ R_4-\text{C}-\text{C}-\text{Oalkyl} \\ | \\ \text{NCO} \end{array} \quad \text{(IX)}$$

with an amine of the formula $$\begin{array}{c} R_3-\text{N}-\text{A}-\text{CN} \\ | \\ \text{H} \end{array} \quad \text{(X)}$$

or a hydrochloride salt of the amine of formula X in the presence of triethylamine. The resulting compound is taken up in ethanol, treated with base such as sodium hydroxide, and the acidified to precipitate the acid of formula VIII.

It is also possible to prepare the activated ester form of the compound of formula VIII without employing the acid of formula VIII as an intermediate. For example, the protected α-amino acid of formula VII is converted to the desired ester, the α-amino protecting group is removed as described above, and the resulting compound is treated with phosgene to yield the corresponding isocyanate. This isocyanate is then reacted with the amine of formula X to yield the desired acylating agent.

The compound of formula I wherein $R_1$ is either hydrogen or methoxy and X is pyridinium or carbamoyl substituted pyridinium are prepared by reacting the compound of the formula (Ib)

with a pyridine or carbamoyl substituted pyridine in a polar solvent such as water and in the presence of a catalyst such as an alkali metal thiocyanate. U.S. Pat. No. 3,792,047 and German Offenlegungsschrift 2,234,280 both disclose methods for reacting a cephalosporin so as to replace an acetoxy group with a pyridinium group.

Also, the compounds of formula I where $R_1$ is either hydrogen or methoxy and X is heterothio can be prepared by reacting the compound of formula Ib with a mercaptan of the formula $$\text{hetero}-\text{S}-\text{H} \quad \text{(XI)}$$

or an alkali metal (preferably sodium) mercaptan salt of the formula $$\text{hetero-S-alkali metal} \quad \text{(XII)}$$

Methods for displacing the acetoxy group of a cephalosporin by a heterothio group are taught in various U.S. patents including U.S. Pat. Nos. 3,855,213; 3,890,309; 3,892,737; etc.

The compounds of formula I wherein R is lower alkyl, phenyl-lower alkyl, trihaloethyl, diphenyl-lower alkyl, or the acyloxymethyl group $$\begin{array}{c} R_5 \quad \text{O} \\ | \quad \| \\ -\text{CH}-\text{O}-\text{C}-R_6 \end{array}$$

may be obtained by reacting the 7-amino cephalosporin of formula VI either before or after the acylation of the 7-amino substituent with one or two moles of a compound of the formula (XIII) halo-R or (XIV) R=N$^+$=N$^-$ wherein halo is preferably chlorine or bromine in an inert solvent such as dimethylformamide, acetone, dioxane, benzene, or the like at about ambient temperature or below.

Similarly, the compounds of formula I wherein R is tri(lower alkyl)silyl are obtained by introducing such groups onto the cephalosporanic acid moiety either before or after the acylation reaction.

The carboxylate salts of the compounds of formula I are formed by reacting the carboxyl group of the cephalosporanic acid moiety, i.e. R is hydrogen, with any of the salt forming ions described above.

It will be appreciated that the compounds of formula I are optically active due to the presence of an asymmetric carbon atom represented as C* in the preceding formulas. By selection of the appropriate starting material it is possible to obtain the compounds of formula I as a mixture of optically active isomers or isolated as a single isomer. The various isomers as well as their mixtures are within the scope of this invention. Also, a second asymmetric carbon atom can be present by virtue of the —A—CN substituent in the acyl side chain, for example, wherein $$\begin{array}{c} \text{CH}_3 \\ | \\ -\text{A}-\text{CN is} -\overset{\ast}{\text{C}}-\text{CN} \\ | \\ \text{H} \end{array}$$

Preferred compounds of this invention are the acids and alkali metal salts of formula I (i.e. R is hydrogen, sodium, or potassium) wherein X is pyridinium, carbamoyl substituted pyridinium (particularly where the carbamoyl group is in the 4-position), or heterothio; $R_4$ is cyclohexenyl, cyclohexadienyl, phenyl, benzyl, phenethyl, substituted phenyl, benzyl, or phenethyl wherein the substituent is on the phenyl ring and is one or two members selected from chloro, bromo, methyl, ethyl, methoxy, ethoxy and hydroxy, or a substituted or unsubstituted heterocyclic selected from 2-thienyl, 3-thienyl, 2-furyl, 3-furyl, 2-pyridyl, 3-pyridyl and 4-pyridyl wherein the heterocyclic substituent is chloro, bromo, methyl, or ethyl; A is straight or branched chain alkylene of 1 to 4 carbons or

$R_2$ is phenyl or 2-thienyl; and $R_3$ is hydrogen or straight or branched chain alkyl of 1 to 4 carbons.

Also preferred as both final products and intermediates are the compounds of formula I wherein X is

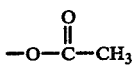

and A, $R_3$ and $R_4$ are as defined above.

The most preferred final compounds are the acids and alkali metal salts of formula I wherein $R_4$ is 2-thienyl, 3-thienyl, phenyl, or 4-hydroxyphenyl; and X is heterothio, particularly wherein X is

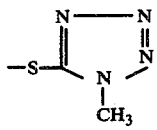

The acid compounds of formula I have a broad spectrum of antibacterial activity against both gram positive and gram negative organisms such as *Staphylococcus aureus, Salmonella schottmuelleri, Pseudomonas aeruginosa, Proteus rettgeri, Escherichia coli, Enterobacter hafniae, Enterobacter cloacae, Klebsiella pneumoniae, Serratia marcescens,* etc. They may be used as antibacterial agents to combat infections due to organisms such as those named above, and in general may be utilized in a manner similar to cephalothin and other cephalosporins. For example, a compound of formula I or a physiologically acceptable salt thereof may be used in various animal species in an amount of about 1 to 100 mg./kg., daily, orally or parenterally, in single or two to four divided doses to treat infections of bacterial origin, e.g., 5.0 mg./kg. in mice.

Up to about 600 mg. of an acid compound of formula I or a physiologically acceptable salt thereof may be incorporated in an oral dosage form such as tablets, capsules or elixirs or in an injectable form in a sterile aqueous vehicle prepared according to conventional pharmaceutical practice.

Illustrative process details are provided in the examples for the various reactions. All temperatures are on the centigrade scale.

EXAMPLE 1

7β-[[D-[[[(Cyanomethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid (a)

D-2-[[[(4-Methoxyphenyl)methoxy]carbonyl]amino]-2-thiopheneacetic acid 74 g. of D-2-Thienylglycine are dissolved in 940 ml. of water. 37.8 g. of magnesium oxide are added and to this resulting suspension a solution of 107.5 g. of p-methoxybenzyloxycarbonylazide in 940 ml. of dioxane is added with stirring. The mixture is stirred at room temperature for 24 hours. It is then filtered and the filtrate is extracted with 600 ml. of ether. The extract is discarded. The water in dioxane phase is layered over with 600 ml. of ethyl acetate, cooled to 5° and brought to pH 2 with 2N hydrochloric acid. The layers are separated and the aqueous layer is again extracted with 300 ml. of ethyl acetate. The combined ethyl acetate extracts are washed with water, dried with magnesium sulfate, filtered and concentrated. The oily residue crystallizes upon trituration with petroleum ether to yield 118 g. of D-2-[[[(4-methoxyphenyl)methoxy]carbonyl]amino]-2-thiopheneacetic acid; m.p. 84°–94°; $[\alpha]_{20}^D$: $-69°$ (c=1, tetrahydrofuran).

(b)

7β-Amino-3-[[(1-methyl-1H-tetrazole-5-yl)thio]methyl]8-oxo-5-thia-1-azabicyclo[4.2.0]oct-2-ene-2-carboxylic acid To a stirred suspension of 27.2 g. 7-amino cephalosporanic acid (0.1 mole) in 150 ml. of acetone and 100 ml. of H₂O at 0–5° is added 50 ml. of 2N NaOH, with care being taken to keep the pH below 8.5. A solution of 12.7 g. (0.11 mole) of 1-methyl-5-mercapto-1H-tetrazole in 50 ml. of 2N NaOH is added, and the mixture is allowed to warm to room temperature. The stirred mixture is then maintained at 60° (internal temperature) under nitrogen for 3 hours at pH 7–7.5 by the periodic addition of dilute aqueous NaOH. The mixture is cooled in an ice-water bath, and while stirring, 3N HCl is added to adjust the pH to 3.9. Stirring is continued for 15 minutes, and the precipitate is collected by filtration, washed with water, and then acetone, and finally dried to give the desired product as a powder (18.4 g.).

(c)

7β-Amino-3-[[(1-methyl-1H-tetrazol-5-yl)thio]methyl]-8-oxo-5-thia-1-azabicyclo[4.2.0]oct-2-ene-2-carboxylic acid, diphenylmethyl ester A mixture of 16.4 g. (0.05 mole) of the acid product from part (b), 10.3 g. (0.054 mole) p-toluenesulfonic acid monohydrate, 350 ml. of dioxane (dried by passage through basic alumina), and dry CH₃OH is stirred at room temperature under nitrogen for 30 minutes. The clear solution is evaporated to a residue, and H₂O and CH₃OH are removed by four evaporations of 100 ml. quantities of dioxane. Fresh dioxane (300 ml.) is then added to the residue followed by a solution of crystalline diphenyldiazomethane (19.4 g., 0.10 mole) in 150 ml. of dry dimethoxyethane. The mixture is initially shaken vigorously for 10–15 minutes and then stirred at room temperature for 3 hours. Methanol (25 ml.) is added, and the red solution is stirred until it has turned yellow-orange. The solvents are removed in vacuo, and the residue is treated with 400 ml. of CH$_2$Cl$_2$ and a solution of 20 g. of K$_2$HPO$_4$ in 250 ml. of H$_2$O. The CH$_2$Cl$_2$ layer is washed with water and saturated NaCl, and finally dried (MgSO$_4$) to give a residue after removal of the solvent in vacuo. Treatment of the residue with Et$_2$O gives a solid (27 g.). Column chromatography of this solid on silica gel by elution with CHCl$_3$ and then EtOAc-CHCl$_3$ (4:1) provides the desired product as a residue (12.9 g.). Treatment with EtOAc then provides 8.0 g. of the desired product as a pale yellow powder.

(d) 7β-[[D-[[[(4-Methoxyphenyl)methoxy]carbonyl]amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid, diphenylmethyl ester 46.2 g. of 7β-amino-3-[[(1-methyl-1H-tetrazol-5-yl)thio]methyl]-8-oxo-5-thia-1-azabicyclo[4.2.0]oct-2-ene-2-carboxylic acid, diphenylmethyl ester from part (c) are dissolved in 550 ml. of anhydrous methylene chloride. 550 ml. of tetrahydrofuran and 36 g. of D-2-[[[(4-methoxyphenyl)-methoxy]carbonyl]amino]-2-thiopheneacetic acid, from part (a), are added. The reaction solution is cooled to 0° and a solution of 22.5 g. of dicyclohexylcarbodiimide in 150 ml. of anhydrous tetrahydrofuran is added dropwise over the course of 30 minutes. The mixture is then stirred for 90 minutes at 0° and finally 120 minutes at room temperature. The precipitated dicyclohexylurea (21 g.) is filtered off under suction and the filtrate is concentrated. The residue is taken up in a mixture of 1000 ml. of ethyl acetate and 400 ml. of tetrahydrofuran, filtered and the filtrate is washed first with sodium bicarbonate solution and then with water. This is then dried with magnesium sulfate, treated with activated carbon, filtered and the filtrate is then concentrated slowly under vacuum to a small volume. After standing overnight in the refrigerator, the precipitate crystals are filtered under suction to obtain 63.1 g. of 7β-[[D-[[[(4-methoxyphenyl)methoxy]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester; m.p. 130°–131° (dec.). [α]$_{20}^D$: −117° (c=1, tetrahydrofuran).

(e)
7β-[D-2-Amino-2-(2-thienyl)acetamido]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt (1:1)

62 g. of the diphenylmethyl ester product from part (d) are added to 300 ml. of anisole with stirring. The mixture is cooled to 0° and 750 ml. of trifluoroacetic acid are added slowly. The mixture is stirred for 10 minutes at 0° and the anisole is evaporated at 0.1 mm. of Hg. and 35° bath temperature. The residue is treated with 250 ml. of petroleum ether, then 350 ml. of ether, stirred for one hour, and filtered with suction to yield 46.4 g. of 7β-[D-2-amino-2-(2-thienyl)acetamido]-3-[[(1-methyl-1H-tetrazol-5-yl)thio]-methyl]-8-oxo-5-thia-1-azabicyclo[4.2.0]oct-2-ene-2-carboxylic acid, trifluoroacetic acid salt (1:1); m.p. 138°–139° (dec.).

(f)
7β-[[(D-[[[(Cyanomethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid 1.16 g. (0.002 mole) of the trifluoroacetic acid salt product of part (e) are suspended in 25 ml. of methylene chloride and brought into solution by the addition of 0.53 ml. of triethylamine. To the resulting clear solution at 0–5° is added dropwise, slowly, a toluene solution of 0.0022 mole of isocyanatoacetonitrile (produced by reacting cyanomethylamine hydrochloride and phosgene in boiling toluene). After stirring for 1 hour at room temperature, the solution, from which oily drops have separated, is concentrated under vacuum. The residue is dissolved in 50 ml. of water, adjusted to pH 6.5 with sodium bicarbonate solution and the turbid solution is extracted with ethyl acetate. The aqueous phase is filtered through Hyflo and the filtrate is acidified to ph 1.5 with 2N hydrochloric acid to yield 0.5 g. of 7β-[[D-[[[(cyanomethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid; m.p. 138°–160° (dec.).

An aqueous equimolar solution of this acid and sodium bicarbonate is lyophilized to yield 7β-[[D-[[[(cyanomethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid; m. p. 138°–160° (dec.).

An aqueous equimolar solution of this acid and sodium bicarbonate is lyophilized to yield 7β-[[D-[[[(cyanomethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt; m.p. 179°–183°.

EXAMPLE 2

7β[[L-[[[(Cyanomethyl)amino]carbonyl]amino]-2-thienylacetyl]-amino]-3-[[(1-methyl-1H-tetrazol-5-yl)thio]methyl]-8-oxo-5-thia-1-azabicyclo[4.2.0]oct-2-ene-2-carboxylic acid (a)
L-2-[[[(4-Methoxyphenyl)methoxy]carbonyl]amino]-2-thiopheneacetic acid L-2-Thienylglycine and p-methoxybenzyloxycarbonylazide are reacted according to the procedure of example 1(a) to yield L-2-[[[(4-methoxyphenyl)methoxy]carbonyl]amino]-2-thiopheneacetic acid; m.p. 97°–98°; [α]$_D^{25}$: +68° (c=1, tetrahydrofuran).

(b)

7β-[[L-[[[ (4-Methoxyphenyl) methoxy]carbonyl]-amino]]-2-thienylacetyl]amino] - 3 - [[(1-methyl-1H-tetrazol-5-yl)thio]methyl]-8-oxo-5-thia-1-azabicyclo[4.2.0]oct-2-ene-2-carboxylic acid, diphenylmethyl ester.

4.6 g. of L-2-[[[(4-methoxyphenyl)methoxy]carbonyl]-amino]-2-thiopheneacetic acid from part (a) and 5.9 g. of 7β-amino-3-[[(1-methyl-1H-tetrazol-5-yl)thio]methyl]-8-oxo-5-thia - 1 - azabicyclo[4.2.0]oct-2-ene-2-carboxylic acid, diphenylmethyl ester from example 1(c) are reacted according to the procedure of example 1(d) to yield 8.4 g. of 7β[[L-[[[4-methoxyphenyl)methoxy]carbonyl]amino]-2-thienylacetyl]amino]-3-[[(1-methyl-1H-tetrazol-5-yl)thio]methyl]-8-oxo - 5 - thia-1-azabicyclo[4.2.0]oct-2-ene-2-carboxylic acid, diphenylmethyl ester which after concentration and treating with ether is obtained in amorphous form.

(c)

7β-[L-2-Amino-2-(2-thienyl)acetamido]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt (1:1)

1.6 g. of the diphenylmethyl ester product from part (b) are treated with trifluoroacetic acid and anisole according to the procedure of example 1(e) to yield 1.1 g. of 7β-[L-2-amino-2-(2-thienyl)acetamido]-3-[[(1-methyl-1H-tetrazol-5-yl)-thio]methyl]-8-oxo-5-thia-1-azabicyclo[4.2.0]oct-2-ene-2-carboxylic acid, trifluoroacetic acid salt (1:1); m.p. 127°–131° (dec.).

(d)

7β-[[L-[[[(Cyanomethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid 2.9 g (0.005 mole) of the trifluoroacetic acid salt product from part (c) is reacted with isocyanatoacetonitrile according to the procedure of example 1(f) to yield 7β-[[L-[[[(cyanomethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid.

An aqueous equimolar solution of this acid and sodium bicarbonate is lyophilized to yield 7β-[[L-[[[(cyanomethyl)amino]carbonyl]amino]-2-thienylacetyl-]amino]-3-[[(1-methyl - 1H - tetrazol-5-yl)thio]methyl]-8-oxo-5-thia-1-azabicyclo[4.2.0]oct-2-ene-2-carboxylic acid, sodium salt.

EXAMPLE 3

7β-[[D-[[[(Cyanomethyl)amino]carbonyl]amino]-phenylacetyl]-amino]-3-[[(1-methyl-1H-tetrazol-5-yl)thio]methyl]-8-oxo-5-thia-1-azabicyclo[4.2.0]oct-2-ene-2-carboxylic acid (a)

D-2-[[[(4-Methoxyphenyl)methoxy]carbonyl]amino]-phenyl-acetic acid

D-2-Phenylglycine and p-methoxybenzyloxycarbonylazide are reacted according to the procedure of example 1(a) to yield D-2-[[[(4-methoxyphenyl)methoxyphenyl)methoxy]carbonyl]amino]-phenylacetic acid.

(b)

7 β-[[D-[[[(4 - Methoxyphenyl)methoxy]carbonyl]-aminio]phenyl]acetyl]amino] - 3 - [[(1-methyl-1H-tetrazol-5-yl)thia]-8-oxo-5-thia-1-azabicyclo[4.2.0]oct-2-ene-2-carboxylic acid, diphenylmethyl ester 12 g. (.025 mole) of 7β-Amino-3-[[(1-methyl-1H-tetrazol - 5 - yl)thio]methyl]-8-oxo-5-thia-1-azabicyclo[4.2.0]oct-2-ene-2-carboxylic acid, diphenylmethyl ester from example 1(c) and 7.7 g. (.025 mole) of D-2-[[[(4-methoxyphenyl)methoxy] - carbonyl]amino]-phenylacetic acid from part (a) are reacted in the presence of 6.2 g. (.025 mole) of dicyclohexylcarbodiimide according to the procedure of example 1(d) to yield 16 g. of light beige 7β-[[D-[[[4-methoxyphenyl)methoxy]carbonyl]amino]phenylacetyl]amino]-3-[[(1-methyl-1H-tetrazol-5-yl)thio]methyl]-8-oxo-5-thia - 1 - azabicyclo[4.2.0]oct-2-ene-2-carboxylic acid, diphenylmethyl ester; m.p. 147° (dec.).

(c)

7β-[D-2-Amino--2-phenylacetamido]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt (1:1)

16 g. of the diphenylmethyl ester product from part (b) are treated with trifluoroacetic acid and anisole according to the procedure of example 1(e) to yield 10.1 g. of 7β-[D-2-amino-2-phenylacetamido]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt (1:1); m.p. 128°–130° (dec.).

(d)

7β-[[D-[[[(Cyanomethyl)amino]carbonyl]amino]-phenylacetyl]-amino]-3-[[(1-methyl-1H-tetrazol-5-yl)thiolmethyl]-8-oxo-5-thia-1-azabicyclo[4.2.0.]oct-2-ene-2-carboxylic acid 0.48 g. (0.002 mole) of the trifluoroacetic acid salt product from part (c) is reacted with isocyanatoacetonitrile according to the procedure of example 1(f) to yield 7β-[[D-[[[(cyanomethyl)amino]carbonyl]amino]-phenylacetyl -amino]-3-[[(1-methyl-1H-tetrazol-5-yl)thio]methyl]-8-oxo-5-thia-1-azabicyclo[4.2.0]oct-2-ene-2-carboxylic acid as light yellow fine crystals; m.p. 98°.

Similarly, by following the above procedure but substituting L-2-phenylglycine for the D-2-phenylglycine in part (a), one obtains 7β-[[L-[[[(cyanomethyl)amino]-carbonyl]amino]phenylacetyl]amino]-3-[[(1-methyl-1H-tetrazol-5-yl)thio]methyl]-8-oxo-5-thia-1-azabicyclo[4.2.0]oct-2-ene-2-carboxylic acid.

EXAMPLE 4

7β-[[D-[[[(Cyanomethyl)amino]carbonyl]amino]-phenylacetyl]-amino]-3-[[(1-methyl-1H-tetrazol-5-yl)thio]methyl]-8-oxo-5-thia-1-azabicyclo[4.2.0]oct-2-ene-2-carboxylic acid, potassium salt, trihydrate An aqueous equimolar solution of 7β-[[D-[[[-(cyanomethyl)amino]carbonyl]amino]phenylacetyl]-amino]-3-[[(1-methyl-1H-tetrazol-5-yl)thio]methyl]-8-oxo-5-thia-1-azabicyclo[4.2.0]oct-2-ene-2-carboxylic acid from example 3 and potassium bicarbonate is lyophilized to yield 7β-[[D[[[(cyanomethyl)amino]carbonyl]amino]phenylacetyl]amino]-3-[[(1-methyl-1H-tetrazol-5-yl)thio]methyl]-8-oxo-5-thia-1-azabicyclo[4.2.0]-oct-2-ene-2-carboxylic acid, potassium salt, trihydrate; m.p. 160°–168° (dec.).

In an analogous manner one can obtain the sodium salt of the acid product of example 3 and the sodium and potassium salts of 7β-[[L-[[[(cyanomethyl)amino]carbonyl]-amino]phenylacetyl]amino]-3-[[(1-methyl-1H-tetrazol-5-yl)-thio]methyl]-8-oxo-5-thia-1-azabicyclo[4.2.0]oct-2-ene-2-carboxylic acid.

EXAMPLE 5

7β-[[D-[[[(D,L-1-Cyanoethyl)amino]carbonyl]amino]-2-thienyl-acetyl]amino]-3-[[(1-methyl-1H-tetrazol-5-yl)thio]methyl]-8-oxo-5-thia-1-azabicyclo[4.2.0]oct-]-ene-2-carboxylic acid (a) D,L-(1-Cyanoethyl)carbomothioic acid, S-phenyl ester 20.4 g. (0.118 mole) of (phenylthio)carbonyl chloride are dissolved in 200 ml. of ether. To this solution is added dropwise at −10° a solution of 0.236 mole of 2-aminopropanonitrile in ether (freshly produced from acetaldehyde by treatment with potassium cyanamide and ammonium chloride). The mixture is stirred overnight, filtered and the filtrate is concentrated. Petroleum ether is added to the residue which crystallizes slowly. 12.9 g. of crude product are obtained. Recrystallization from a small amount of toluene yields 10 g. of D,L-(1-cyanoethyl)carbamothioic acid, S-phenyl ester; m.p. 108°–111°.

(b) 7β-[[D-[[[(D,L-1-Cyanoethyl)amino]amino]carbonyl]amino]-2-thienylacetyl]amino]-3-[[(1-methyl-1H-tetrazol-5-yl)-thio]methyl]-8-oxo-5-thia-1-azabicyclo[4.2.0]oct-2-ene-2-carboxylic acid 1.16 g. (0.002 mole) of the trifluoroacetic acid salt product from example 1(e) are suspended in 10 ml. of absolute dioxane, cooled to 10° and 0.82 ml. (0.006 mole) of triethylamine are added. 0.496 g. (0.0024 mole) of D,L-(1-cyanoethyl)carbamothioic acid, S-phenyl ester from part (a) is added and the solution is stirred for six hours at 0°. The solution is poured into ether and the resulting precipitate is isolated. After drying, it is dissolved in water and the solution is filtered and acidified to yield 7β-[[D-[[[D,L-1-(cyanoethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid as a precipitate.

An aqueous equimolar solution of this acid and sodium bicarbonate is lyophilized to yield 7β-[[D-[[[(D,L-1-cyanoethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt; m.p. 177°–184° (dec.).

In an analogous manner one can obtain 7β[[L-[[[(D,L-1-cyanoethyl)amino]carbonyl]amino]-2-thienylacetyl]amino]-3-[[(1-methyl-1H-tetrazol-5-yi)thio]methyl]-8-oxo-5-thia-1-azabicyclo[4.2.0]oct-2-ene-2-carboxylic acid and its sodium salt.

EXAMPLE 6

7β-[[D-[[[(1-Cyano-1-methylethyl)amino]carbonyl]amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid (a) (1-Cyano-1-methylethyl)carbamothioic acid, S-phenyl ester 3.4 g. (0.04 mole) of 2-amino-2-methylpropanonitrile are dissolved in 10 ml. of dioxane and a solution of 3.2 ml. (0.2 mole) of (phenylthio)carbonyl chloride in 10 ml. of dioxane is added. After stirring for one hour at room temperature, the reaction mixture is filtered, the filtrate is concentrated, and the solid residue is recrystallized from a small amount of toluene to yield 2.7 g of (1-cyano1-methylethyl)carbamothioic acid, S-phenyl ester; m.p. 152°–155°.

(b) 7β-[[D-[[[(1-Cyano-1-methylethyl)amino]carbonyl]amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid 1.1 g. (0.005 mole) of (1-cyano-1-methylethyl)-carbamothioic acid, S-phenyl ester from part (a) and 2.6 g. (0.005 mole) of the trifluoroacetic acid salt product from example 1(e) are reacted according to the procedure of example 5(b) to yield 2.1 g. of 7β-[[D-[[[(1-cyano-1-methyl-ethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid; m.p. 137°–155° (dec.).

An aqueous equimolar solution of this acid and sodium bicarbonate is lyophilized to yield 7β[[D-[[[(1-cyano-1-methylethyl)amino]carbonyl]amino]-2-thienylacetyl]-amino]-3-[[(1-methyl-1H-tetrazol-5-yl)thio]methyl]-8 -oxo-5-thia-1-azabicyclo[4.2.0]oct-2-ene-2-carboxylic acid, sodium salt; m.p. 167°–178° (dec.).

In an analogous manner one can obtain 7β-[[L-[[[(1-cyano-1-methylethyl)amino]carbonyl]amino]-2-thienyl-acetyl]amino]-3-[[(1-methyl-1H-tetrazol-5-yl)thio]-methyl]-8-oxo-5-thia-1-azabicyclo[4.2.0]oct-2-ene-2-carboxylic acid and its sodium salt.

EXAMPLE 7

7β-[[D-[[[(2-Cyanoethyl)amino]carbonyl]amino]-2-thienyl-acetyl]amino]-3-[[(1-methyl-1H-tetrazol-5-yl)thio]methyl]-8-oxo-5-thia-1-azabicyclo[4.2.0]oct-2-ene-2-carboxylic acid (a) (2-Cyanoethyl)carbamothioic acid, S-phenyl ester 3.88 g. (0.03 mole) of 3-aminopropanonitrile fumarate are dissolved in 10 ml. of water and a solution of 3.2 ml. (0.02 mole) of (phenylthio)carbonyl chloride in 30 ml. of dioxane is added dropwise. By the simultaneous addition of 2N sodium hydroxide (about 22 ml.) the pH of the reaction mixture is maintained at about 8. The mixture is stirred an additional 30 minutes, diluted with water, and the resulting precipitate (3.3 g.) is crystallized from a small amount of toluene to yield 2.9 g. of (2-cyanoethyl) carbamothioic acid, S-phenyl ester; m.p 86°–90°.

(b)
7β-[[D-[[[(2-Cyanoethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid 0.582 g. (0.001 mole) of the trifluoroacetic acid salt product from example 1(e) and 0.248 g. (0.0012 mole) of (2-cyanoethyl)carbamothioic acid, S-phenyl ester from part (a) are reacted according to the procedure of example 5(b) to yield 0.35 g. of 7β-[[D-[[[(2-cyanoethyl)-amino]carbonyl]amino]-2-thienylacetyl]amino]-3[[(1-methyl-1H-tetrazol-5-yl)thio]methyl]-8-oxo-5-thia-1-azabicyclo-[4.2.0]oct-2-ene-2-carboxylic acid; m.p. 145°-148° (dec.).

An aqueous equimolar solution of this acid and sodium bicarbonate is lyophilized to yield 7β-[[D-[[[(2-cyanoethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt; m.p. 173°-181°.

In an analogous manner one obtains, 7β-[[L-[[[(2-cyanoethyl)amino]carbonyl]amino]-2-thienylacetyl]-amino]-3-[[(1-methyl-1H-tetrazol-5-yl)thio]methyl]-8-oxo-5-thia-1-azabicyclo[4.2.0]oct-2-ene-2-carboxylic acid and its sodium salt.

EXAMPLE 8

7β-[[D-[[[(DL-Cyanophenylmethyl)amino]carbonyl]amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid (a) D,L-(Cyanophenylmethyl)carbamothioic acid, S-phenyl ester A solution of 6.1 g. (0.036 mole) of α-cyanobenzylamine in 13 ml. of water is added to a solution of 4.8 ml. (0.03 mole) of (phenylthio)carbonyl chloride dissolved in 39 ml. of dioxane. The mixture is stirred vigorously and a 2N sodium hydroxide solution is added dropwise at room temperature until a weakly alkaline pH is attained (approximately 35 to 40ml.). Crystals precipitate and the solution is stirred for two more hours and then filtered under suction. 8.5 g. of crude product are obtained. Recrystallization from approximately 70 ml. of toluene yields 6.8 g. of D,L-(cyanophenylmethyl)carbamothioic acid, S-phenyl ester; m.p. 145°-150°.

(b)
7β-[[D-[[[(D,L-Cyanophenylmethyl)amino]carbonyl]amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid 1.16 g. (0.002 mole) of the trifluoroacetic acid salt from example 1(e) are suspended in 16 ml. of anhydrous acetonitrile and brought into solution by the addition of 2 ml. of bis(trimethylsilyl)acetamide. 0.644 g. (0.0024 mole) of D,L-(cyanophenylmethyl)carbamothioic acid, S-phenyl ester from part (a) are added to the solution and the mixture is stirred overnight at room temperature. 20 ml. of water and 2 ml. of 2N hydrochloric acid are added so that the aqueous phase is at a pH of 2. The aqueous phase is then extracted three times with ethyl acetate and the resulting organic phase is dried with magnesium sulfate and concentrated. Trituration with ether yields a solid residue which is purified by precipitation from ethyl acetate/ether to yield 0.4 g. of 7β-[[D-[[[D,L-cyanophenylmethyl)amino]carbonyl]amino]-2-thienylacetyl]amino]-3-[[(1-methyl-1H-tetrazol-5-yl)thio]-8-oxo-5-thia-1-azabicyclo[4.2.0]oct-2-ene-2-carboxylic acid; m.p. 151°-165° (dec.).

An aqueous equimolar solution of this acid and sodium bicarbonate is lyophilized to yield 7β-[[D-[[[D,L-cyanophenylmethyl)amino] carbonyl] amino]-2-thienylacetyl]amino]-3-[[(1-methyl-1H-tetrazol-5-yl)thio]methyl]-8-oxo-5-thia-1-azabicyclo-[4.2.0]oct-2-ene-2-carboxylic acid, sodium salt.

In an analogous manner one obtains, 7β-[[L-[[[(D,L-cyanophenylmethyl)amino] carbonyl] amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid and its sodium salt.

EXAMPLE 9

7β-[[D-[[[[DL-Cyano-(2-thienyl)methyl]amino]carbonyl]amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid (a)
D-2-[[[(4-Methoxyphenyl)methoxy]carbonyl]amino]-2-thiophene-acetic acid, 4-nitrophenyl ester 64.8 g. (0.2 mole) of D-2-[[[(4-methoxyphenyl)methoxy]-carbonyl]amino]-2-thiopheneacetic acid from example 1(a) are dissolved in 330 ml. of anhydrous tetrahydrofuran. A solution of 28 g. (0.2 mole) of 4-nitrophenol in 330 ml. of tetrahydrofuran is added. The mixture is cooled to 0° and a solution of 41.4 g. (0.2 mol) of dicyclohexylcarbodiimide in 134 ml. of tetrahydrofuran is added dropwise over a perod of 90 minutes. The mixture is stirred overnight at 0°. It is then filtered and the filtrate is concentrated to yield 90 g. of crude product. Crystallization from toluene yields D-2-[[[(4-methoxyphenyl)-methoxy]carbonyl]amino]-2thiopheneacetic acid, 4-nitrophenyl ester; m.p. 98°-105° (dec.).

(b) D-2-Amino-2-thiopheneacetic acid, 4-nitrophenyl ester, hydrochloride 63.8 g. of D-2-[[[(4-methoxyphenyl)methoxy]carbonyl]-amino]-2-thiopheneacetic acid, 4-nitrophenyl ester from part (a) are added at 0° to 300 ml. of a saturated solution of HCl gas in glacial acetic acid. The nitrophenyl ester from part (a) goes into solution and shortly thereafter the hydrochloride salt precipitates as a thick crystalline slurry. The hydrochloride salt is filtered under suction and additional hydrochloride salt is obtained from the filtrate by concentrating to give a combined yield of 46.2 g. of D-2-amino-2-thiopheneacetic acid, 4-nitrophenyl ester hydrochloride; m.p. 173°-176° (dec.).

(c) D-2-Isocyanato-2-thiopheneacetic acid, 4-nitrophenyl ester

Phosgene is passed into as boiling suspension of 21 g. of D-2-amino-2-thiopheneacetic acid, 4-nitrophenyl ester, hydrochloride in 300 ml. of toluene until a clear solution results. After concentrating, D-2-isocyanato-2-thiopheneacetic acid, 4-nitrophenyl ester remains as an oily residue.

(d) D-2-[[[[DL-Cyano-(2-thienyl methyl]amino]carbonyl]amino]-2-thiopheneacetic acid, 4-nitrophenyl ester 1.38 g. of DL-2-[cyano(amino)methyl]thiophene dissolved in 10 ml. of absolute tetrahydrofuran is added dropwise at 5° to a solution of 3.55 g. (0.01 mole) of D-2-isocyanato-2-thiopheneacetic acid, 4-nitrophenyl ester, from part (c), in 20 ml. of absolute tetrahydrofuran. After stirring for one hour, the solvent is removed to yield 4.4 g. of a beige foam which is recrystallized from cyclohexane/benzene to yield D-2-[[[[D,L-cyano-(2-thienyl)methyl]amino]carbonyl]amino]-2-thiopheneacetic acid, 4-nitrophenyl ester; m.p. 142°.

(e)

7β-[[D-[[[[DL-Cyano-(2-thienyl)methyl]amino]carbonyl]amino]-2-thienylacetyl]amino]-3-[[(1-methyl-1H-tetrazol-5-yl)thiol]-methyl]-8-oxo-5-thia-1-azabicyclo[4.2.0]oct-2-ene-2-carboxylic acid, diphenylmethyl ester 2.21 g. (0.005 mole) of D-2-[[[[D,L-cyano-(2-thienyl)methyl]amino]carbonyl]amino]-2-thiopheneacetic acid, 4-nitrophenyl ester, from part (d), together with 1.5 g. of 1-hydrobenzotriazole and 2.5 g. of 7β-amino-3-[[(1-methyl-1H-tetrazol-5-yl)thio]methyl]-8-oxo-5-thia-1-azabicyclo [4.2.0]oct-2-ene-2-carboxylic acid, diphenylmethyl ester, from example 1(c), are dissolved in 30 ml. of dimethylacetamide and stirred for 12 hours at from 5° to 10°. The reaction mixture is then poured into 300 ml. of water, this mixture is then extracted three times with 50 ml. portions of ethylacetate. The ethylacetate extracts are washed successively with 50 ml. portions of 2N sodium bicarbonate solution, water, and sodium chloride solution, dried, and concentrated to 20 ml. 20 ml. of ether are added precipitating as a light beige powder 7β-[[D-[[[[D,L-cyano-(2-thienyl)methyl]amino]carbonyl]amino]-2-thienylacetyl]-amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester; m.p. 152°-155° (dec.).

(f)

7β-[[D-[[[[DL-Cyano-(2-thienyl)methyl]amino]carbonyl]amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid 2.7 g. of the diphenylmethyl ester product from part (e) are stirred in 50 ml. of trifluoroacetic acid/anisole (4:1) for 10 minutes at −10°. The trifluoroacetic acid and anisole are evaporated under vacuum and the brown syrup residue is triturated with ether solidifying crude product. This material is precipitated three times from tetrahydrofuran/ether to yield as a beige powder 7β-[[D-[[[[D,L-cyano-(2-thienyl)methyl]amino]-carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid; 161°-167° (dec.).

An aqueous equimolar solution of this acid and potassium bicarbonate is lyophilized to yield as a beige powder 7β-[[D-[[[[D,L-cyano-(2-thienyl)methyl]amino]carbonyl]amino[-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, potassium salt; 165°-169° (dec.). Substituting sodium bicarbonate for the potassium bicarbonate one obtains the corresponding sodium salt.

In an analogous manner one obtains 7β-[[L-[[[[D,L-cyano-2-thienyl)methyl]amino]carbonyl]amino]-2-thienylacetyl]-amino]-3-[[(1methyl-1H-tetrazol-5-yl)thio]methyl]-8-oxo-5-thia-1-azabicyclo[4.2.0]oct-2-ene-2-carboxylic acid and its sodium or potassium salt.

EXAMPLE 10

7α-Methoxy-7β-[[D,L-[[[(cyanomethyl)amino]carbonyl]amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid (a)

7α-Methoxy-7β-[[D,L-[[[(4-methoxyphenyl)methoxy]-carbonyl]-amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 2.41 g. (0.0075 mole) of D,L-2-[[[(4-methoxyphenyl)-methoxy]carbonyl]amino]-2-thiopheneacetic acid (prepared according to the procedure of example 1(a)) is dissolved in 50 ml. of dry methylene chloride, the solution is cooled in an ice bath to 0°-5°, and 0.969 g. (0.0075 mole) of diisopropylethylamine and isobutylchloroformate are added to the cold solution. After 10 minutes, 3.28 g. (0.00625 mole) of 7β-amino-7α-methoxy-3-[[(1-methyl-1H-tetrazol-5-yl)thio]methyl]-8-oxo-5-thia-1-azabicyclo[4.2.0]oct-2-ene-2-carboxylic acid, diphenylmethyl ester is added to the reaction mixture and the ice bath is removed. Following three hours of stirring at room temperature, a second portion of mixed anhydride is prepared in a separate flask using the procedure described above. This solution is added to the reaction mixture and after 4.5 hours another batch of mixed anhydride prepared using half the quantities set forth above is added to the main reaction mixture. Stirring is continued at room temperature for 12 hours and the reaction mixture is then diluted with methylene chloride and washed with water, saturated aqueous sodium bicarbonate solution, and water. The organic layer is dried over sodium sulfate and the solvent is removed in vacuo to yield a foam. This crude product is chromatographed on silica gel (200 g., 60–200 mesh) and the desired product is eluted with 9:1 and 4:1 methylene chloride:ethyl acetate. The oily product is precipitated as a powder from a methylene chloride-ether mixture and dried over phosphorous pentoxide in vacuo to yield 3.81 g. of 7α-methoxy-7β-[[D,L-[[[(4-methoxyphenyl)-methoxy]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester. Alternatively, the titled compound can be obtained by the following procedure.

129 mg. (0.4 mmole) of D,L-2-[[[(4-methoxyphenyl)-methoxy]carbonyl]amino]-2-thiopheneacetic acid is dissolved in 2 ml. of anhydrous methylene chloride and 47 mg. (0.2 mmole) of dicyclohexylcarbodiimide is added. The mixture is stirred for 15 minutes at room temperature during which time colorless dicyclohexylurea crystallizes. The suspension is directly filtered into a stirring solution of 77 mg. (0.147 mmole) of 7β-amino-7α-methoxy-3-[[(1-methyl-1H-tetrazol-5-yl)thio]methyl]-8-oxo-5-thia-1-azabicyclo[4.2.0]-oct-2-ene-2-carboxylic acid, diphenylmethyl ester in 1 ml. of methylene chloride. After stirring at room temperature for 19 hours, the mixture is diluted with methylene chloride, washed with pH 7.4 buffer, and dried over sodium sulfate. Removal of solvent under reduced pressure yields a crude oil which is chromatographed on preparative thin layer chromatography silica gel plates developed in a 4:1 chloroform:ethyl acetate mixture. The desired product (58 mg.) is isolated as an oil.

(b) 7α-Methoxy-7β-[D,L-2-amino-2-(2-thienyl)acetamido]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt (1:1)

The diphenylmethyl ester product from part (a) is reacted with trifluoroacetic acid in the presence of anisole according to the procedure of example 1 (e) to yield the titled compound.

(c) 7α-Methoxy-7β-[[D,L-[[[(cyanomethyl)amino]carbonyl]amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid The trifluoroacetic acid salt product of part (b) is suspended in methylene chloride and triethylamine and reacted with isocyanatoacetonitrile according to the procedure of example 1 (f) to yield 7α-methoxy-7β-[[D,L-[[[(cyanomethyl)-amino]carbonyl]amino]-2-thienylacetyl]amino]-3-[[(1-methyl-1-H-tetrazol-5-yl)thio]methyl]-8-oxo-5-thia-1-azabicyclo[4.2.0]oct-2-ene-2-carboxylic acid.

EXAMPLE 11

7α-Methoxy-7β-[[D-[[[(cyanomethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt The product of example 10 is subjected to high pressure liquid chromatograph fractionation to obtain 7α-methoxy-7β-[[D-[[[(cyanomethyl)amino]carbonyl]amino]-2-thienylacetyl]amino]-3-[[(1-methyl-1H-tetrazol-5-yl)thio]methyl]-8oxo-5-thia-1-azabicyclo[4.2.0]oct-2-ene-2-carboxylic acid.

An equimolar aqueous solution of this acid and sodium bicarbonate is lyophilized to yield 7α-methoxy-7β-[[D-[[[(cyanomethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt; m.p. 167°–174° (dec.).

EXAMPLE 12

7α-Methoxy-7β-[[D,L-[[D,L-1-cyanoethyl)amino]carbonyl]amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid An equimolar amount of the trifluoroacetic acid salt product from Example 10(b) and D,L-(1-cyanoethyl)-carbamothioic acid, S-phenyl ester from Example 5(a) are reacted according to the procedure set forth in Example 5(b) to yield 7α-methoxy-7β-[[D,L-[[[-cyanoethyl)amino]carbonyl]amino]-2-thienyl-acetyl]-amino]-3-[[(1-methyl - 1H - tetrazol-5-yl)thio]methyl]-8-oxo-5-thia-1-azabicyclo[4.2.0]oct-2-ene-2-carboxylic acid.

EXAMPLE 13

7α-Methoxy-7β-[[D-[[[(cyanomethyl)amino]carbonyl]-amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid, sodium salt The compound of example 11 can also be prepared by the following procedure.

1.5 g. of 7β-amino-7α-methoxy-3-[[(1-methyl-1H-tetrazol-5-yl)thio]methyl]-8-oxo-5-thia-1-azabicyclo[4.2.0]-oct-2-ene-2-carboxylic acid, potassium salt are dissolved in 11 ml. of a mixture of dioxane/acetone (1:1). 1.9 ml. of bistrimethylsilyl acetamide are added, the solution is cooled to 0° and 7.5 ml. of propylene oxide are added (Solution A).

0.91 g. D-2-[[[(cyanomethyl)amino]carbonyl]amino]-2-thiopheneacetic acid (prepared by reacting D-2-thienylglycine and isocyanatoacetonitrile) are dissolved in 11 ml. of acetonitrile. The mixture is cooled to −20° and while at this temperature a solution of 0.28 ml. of thionyl chloride in 5 ml. of acetonitrile is added. The resulting solution is stirred at −20° for twenty minutes (Solution B).

Solution B is added to solution A while both are at −20° and the resulting mixture is stirred for forty minutes at −20°. Meanwhile an additional portion of solution B prepared form 0.45 g. of D-2-[[[(cyanomethyl)amino] carbonyl] -amino -2- thiopheneacetic acid and at the end of the forty minutes of stirring at −20° this additional amount of solution B is added to the stirred mixture of solutions A and B. The resulting mixture is stirred for an additional forty minutes at −20°. The mixture is then diluted with approximately 50 ml. of ethyl acetate and 10 ml. of water. This diluted mixture is stirred for five minutes and the layers are separated. The organic phase is shaken two more times with water, dried with magnesium sulfate, filtered, and the filtrate is concentrated under a vacuum. The residue is taken up in ether to yield 1 g. of 7α-methoxy-7β7β[D-[[[(cyano methyl)amino]carbonyl]amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid.

This acid is dissolved in 7.5 ml. of methanol and the solution is clarified with activated charcoal. 2.5 ml. of 2N sodium ethyl hexanoate solution are added followed by the addition of ether to yield 0.6 g. of 7α-methoxy-7 β-[[D-[[[(cyanomethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt.

EXAMPLE 14

7β[[D-[[[(Cyanomethyl)methylamino]carbonly]amino]phenylacetyl]amino]-3-[[(1-methyl-1H-tetrazol-5-yl)thio]methyl]-8-oxo-5-thia-1-azabicyclo[4.2.0]oct-2ene-2-carboxylic acid (a)
D-[[[(Cyanomethyl)methylamino]carbonyl]amino]-phenylacetic acid, ethyl ester An equimolar mixture of methylaminoacetonitrile hydrochloride salt suspended in tetrahydrofuran and D-isocyanatophenylacetic acid, ethyl ester is prepared. Triethylamine is added and the reaction mixture is stirred at room temperature for 24 hours, filtered, and concentrated to yield D-[[[(cyanomethyl)methylamino]carbonyl]amino]phenylacetic acid ethyl ester as a viscous oil.

(b)
D-[[[(Cyanomethyl)methylamino]carbonyl]amino]-phenylacetic acid 15.3 g. of the ethyl ester product from part (a) are added to 30 ml. of ethanol and then this is added to 42 ml. of a 2N sodium hydroxide solution. The resulting mixture is stirred at room temperature for 1 hour, the ethanol is distilled off under vacuum and the residue is acidified with 2N hydrochloric acid. An amorphous precipitate is filtered off, the filtrate is saturated with sodium chloride and extracted several times with ethyl acetate. The ethyl acetate extracts are washed once with water, dried with magnesium sulfate and concentrated. The residue is triturated with ether to yield D-[[[(cyanomethyl)methylamino]carbonyl]amino]phenylacetic acid in solid amorphous form.

(c)

7β-[[D-[[[(Cyanomethyl)methylamino]carbonyl]amino]phenyl-acetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 7β-Amino-3-[[(1-methyl-1H-tetrazol-5-yl)thio]methyl]-8-oxo-5-thia-1-azabicyclo[4.2.0]oct-2-ene-2-carboxylic acid, diphenylmethyl ester from example 1(c) is reacted with D-[[[(cyanomethyl)methylamino]carbonyl]amino]phenylacetic acid from part (b) in the presence of dicyclohexylcarbodiimide according to the procedure of example 1(d) to yield the titled compound in an amorphous form.

(d)

7β-[[D-[[[(Cyanomethyl)methylamino]carbonyl]amino]phenylacetyl]amino]-3-[[(1-methyl-1H-tetrazol-5-yl)thio]-methyl]-8-oxo-5-thia-1-azabicyclo[4.2.0]oct-2-ene-2-carboxylic acid The diphenylmethyl ester from part (c) is treated with trifluoroacetic acid and anisole according to the procedure of example 1(e) to yield 7β-[[D-[[[(cyanomethyl)-methylamino]carbonyl]amino]phenylacetyl]amino]-3-[[(1-methyl-1H-tetrazol-5-yl)thio]methyl]-8-oxo-5-thia-1-azabicyclo-[4.2.0]oct-2-ene-2-carboxylic acid.

Similarly, by substituting 7α-methoxy-7β-amino-3-[[(1-methyl-1H-tetrazol-5-yl)thio]methyl]-8-oxo-5-thia-1-azabicyclo[4.2.0]oct-2-ene-2-carboxylic acid, diphenylmethyl ester for the desmethoxy compound in part (c), one obtains 7α-methoxy7β-[[D-[[[(cyanomethyl)-methyamino]carbonyl]amino]-phenylacetyl]amino]-3-[[(1-methyl-1H-tetrazol-5-yl)thio]methyl]-8-oxo-5-thia-1-azabicyclo[4.2.0]oct-2-ene-2-carboxylic acid.

The corresponding L isomers are obtained in an analogous manner.

Any of these acid products can be converted to the sodium or potassium salt by lyophilizing an equimolar solution of the acid and sodium or potassium bicarbonate.

EXAMPLE 15

7β-[[D-[[[(Cyanomethyl)methylamino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid 0.291 g. (0.0005 mole) of the trifluoroacetic acid salt product from Example 1(e) are suspended in 4 ml. of acetone, 1 ml. of propylene oxide is added and the mixture is cooled to 0°-5°. After the addition of 0.5 ml. of bistrimethylsilyl acetamide (BSA) a clear solution of the trimethylsilyl ester of the trifluoroacetic acid salt results. To this solution is added with stirring at 0°-5° a solution of 0.0005 moles of (cyanomethyl)methylcarbamoyl chloride in 2 ml. of acetone. The solution is allowed to come to room temperature and is stirred for an additional hour. Then 4 ml. of water are added and the pH of the mixture is adjusted to 8.5. This mixture is extracted twice with ethyl acetate. The aqueous phase is then layered over with fresh ethyl acetate and the pH is adjusted to 2. The ethyl acetate layer is then separated, washed with water, dried over magnesium sulfate and concentrated. Upon triturating the residue with petroleum ether, 7β-[[D-[[[(cyanomethyl)methylamino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid is obtained in a solid form.

Following the above procedure but employing the 7α-methoxy-trifluoroacetic acetic acid salt from example 10(b), one obtains 7α-methoxy-7β-[[D,L-[[[(cyanomethyl)methylamino]-carbonyl]amino]-2-thienylacetyl]amino]-3-[[(1-methyl-1H-tetrazol-5-yl)thio]methyl]-8-oxo-5-thia-1-azabicyclo[4.2.0]-oct-2-ene-2-carboxylic acid.

EXAMPLES 16–70

Following the procedure of examples 1 to 3, 5 to 10, 12 and 15 but employing the trifluoroacetic acid salt shown in Col. I and either the isocyanato compound of Col. II or the carbonyl chloride of Col. III or the carbamothioic acid, S-phenyl ester of Col. IV one obtains the acid product shown in Col V. This compound can be reacted so as to introduce an ester group and yield the compound of Col. VI or can be treated according to the procedure of Example 4 or by other known procedures to yield the corresponding salt.

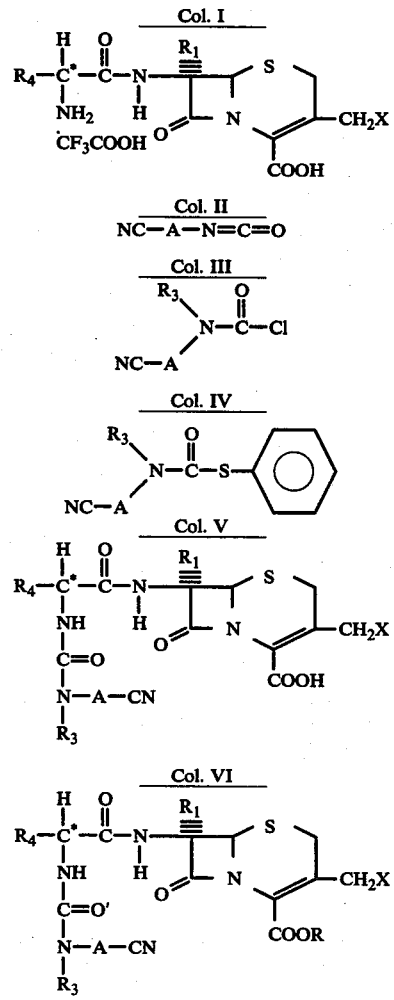

Alternatively, the α-aminocephalosporanic acid ester of Col. VII can be treated with the compound of Col.

II, III, or IV to yield the ester of Col. VI. This ester can then be treated to remove the ester group and yield the cephalosporanic acid of Col. V.

Col. VII $$R_4-\overset{H}{\underset{NH_2}{C^*}}-\overset{O}{C}-N-\overset{R_1}{\underset{H}{C}}-\begin{array}{c}\text{(β-lactam-cephem core)}\\COOR\end{array}-CH_2X$$

| Ex. | $R_4$ | R | $R_1$ | X | A | $R_3$ |
|---|---|---|---|---|---|---|
| 16 | 2-thienyl | $-CH_2-C_6H_5$ | $-H$ | 1-methyl-tetrazol-5-yl-thio | $-(CH_2)_3-$ | $-H$ |
| 17 | 4-chloro-2-thienyl | $-t-C_4H_9$ | $-OCH_3$ | 1-methyl-tetrazol-5-yl-thio | $-CH_2-$ | $-H$ |
| 18 | 5-methyl-2-thienyl | $-t-C_4H_9$ | $-H$ | 1-ethyl-tetrazol-5-yl-thio | $-(CH_2)_4-$ | $-H$ |
| 19 | 2-furyl | $-CH(C_6H_5)_2$ | $-OCH_3$ | 1-methyl-tetrazol-5-yl-thio | $-CH_2-$ | H |
| 20 | 2-furyl | $-CH_2-C_6H_5$ | $-H$ | 1-methyl-tetrazol-5-yl-thio | $-CH_2-$ | $-CH_3$ |
| 21 | 5-chloro-2-furyl | $-CH(C_6H_5)_2$ | $-OCH_3$ | 1-methyl-tetrazol-5-yl-thio | $-(CH_2)_2-$ | $-H$ |
| 22 | 3-methyl-2-furyl | $-CH_2CCl_3$ | $-H$ | 1-methyl-tetrazol-5-yl-thio | $-C(CH_3)_2-$ | $-H$ |
| 23 | 2-furyl | $-CH_2CCl_3$ | $-OCH_3$ | 1-methyl-tetrazol-5-yl-thio | $-CH(CH_3)-$ | $-CH_3$ |
| 24 | 2-furyl | $-t-C_4H_9$ | $-H$ | 1-ethyl-tetrazol-5-yl-thio | 2-thienylidene -CH- | $-H$ |
| 25 | 3-pyridyl | $-CH_2-C_6H_5$ | $-H$ | 1-methyl-tetrazol-5-yl-thio | $-(CH_2)_3-$ | $-C_2H_5$ |
| 26 | 3-pyridyl | $-CH(C_6H_5)_2$ | $-OCH_3$ | tetrazol-5-yl-thio (NH) | $-C(H)(CH_3)-CH_2-CH_2-$ | $-H$ |

-continued

Col. VII

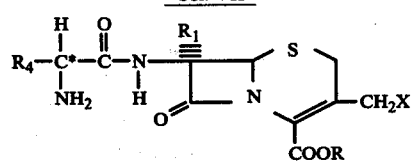

| Ex. | R₄ | R | R₁ | X | A | R₃ |
|---|---|---|---|---|---|---|
| 27 | 3-chloro-4-pyridyl | -t-C₄H₉ | -H | -S-(1-methyltetrazol-5-yl) | -(CH₂)₈- | -H |
| 28 | phenyl | -t-C₄H₉ | -H | -S-(1-methyltetrazol-5-yl) | -(CH₂)₂- | -C₂H₅ |
| 29 | phenyl | -CH(C₆H₅)₂ | -OCH₃ | -S-(1-methyltetrazol-5-yl) | -(CH₂)₄- | -n-C₃H₇ |
| 30 | 3-chlorobenzyl | -CH₂CCl₃ | -H | -S-(1-methyltetrazol-5-yl) | -C(CH₃)₂- | -H |
| 31 | 4-hydroxyphenyl | -CH(C₆H₅)₂ | -H | -S-(1-methyltetrazol-5-yl) | -CH₂- | -H |
| 32 | 4-hydroxyphenyl | -CH(C₆H₅)₂ | -OCH₃ | -S-(1-methyltetrazol-5-yl) | -C(CH₃)₂- | -CH₃ |
| 33 | 4-hydroxybenzyl | -CH₂CCl₃ | -H | -S-(1-methyltetrazol-5-yl) | -CH(C₆H₅)- | -H |
| 34 | 4-methylphenyl | -t-C₄H₉ | -OCH₃ | -S-(1-methyltetrazol-5-yl) | -CH(2-thienyl)- | -H |
| 35 | benzyl | -CH₂C₆H₅ | -H | -S-(1-methyltetrazol-5-yl) | -(CH₂)₄- | -H |
| 36 | 3-methoxyphenyl | -t-C₄H₉ | -H | -S-(1-methyltetrazol-5-yl) | -(CH₂)₃- | -CH₃ |
| 37 | phenyl | -CH₂C₆H₅ | -H | -S-(1-methyltetrazol-5-yl) | -C(CH₃)₂-CH₂-C(CH₃)₂- | -H |

-continued

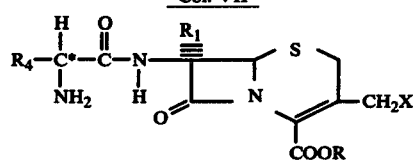

Col. VII

| Ex. | R₄ | R | R₁ | X | A | R₃ |
|---|---|---|---|---|---|---|
| 38 | cyclohexenyl | -t-C₄H₉ | -OCH₃ | -S-(1-methyltetrazol-5-yl) | -CH₂- | -H |
| 39 | cyclohexyl | -CH(C₆H₅)₂ | -H | -S-(1H-tetrazol-5-yl) | -(CH₂)₅- | -H |
| 40 | -C₂H₅ | -CH₃ | -H | -S-(1-methyltetrazol-5-yl) | -CH₂- | -H |
| 41 | 2-thienyl | -t-C₄H₉ | -H | -S-(5-methyl-1,3,4-thiadiazol-2-yl) | -CH₂- | -CH₃ |
| 42 | 2-thienyl | -CH(C₆H₅)₂ | -OCH₃ | -S-(5-methyl-1,3,4-oxadiazol-2-yl) | -C(CH₃)₂- | -H |
| 43 | 2-thienyl | -CH₂CCl₃ | -H | -S-(5-methyl-1,3,4-thiadiazol-2-yl) | -CH(2-thienyl)- | -H |
| 44 | 2-furyl | -CH₂C₆H₅ | -OCH₃ | -S-(5-methyl-1,3,4-thiadiazol-2-yl) | -CH₂- | -CH₃ |
| 45 | 2-furyl | -t-C₄H₉ | -H | -S-(5-methyl-1,3,4-thiadiazol-2-yl) | -CH₂- | -H |
| 46 | C₆H₅- | -CH(C₆H₅)₂ | -OCH₃ | -S-(5-methyl-1,3,4-thiadiazol-2-yl) | -(CH₂)₂- | -H |
| 47 | C₆H₅- | -Si(CH₃)₃ | -H | -S-(5-methyl-1,3,4-thiadiazol-2-yl) | -CH(CH₃)- | -H |
| 48 | HO-C₆H₄- | -t-C₄H₉ | -OCH₃ | -S-(5-methyl-1,3,4-oxadiazol-2-yl) | -CH₂- | -CH₃ |
| 49 | HO-C₆H₄- | -CH₂CCl₃ | -H | -S-(5-methyl-1,3,4-thiadiazol-2-yl) | -CH₂- | -C₂H₅ |
| 50 | C₆H₅- | -t-C₄H₉ | -OCH₃ | -S-(5-methyl-1,3,4-oxadiazol-2-yl) | -(CH₂)₂- | -H |
| 51 | 2-thienyl | -t-C₄H₉ | -H | -S-(4-methylthiazol-2-yl) | -CH₂- | -H |
| 52 | 2-thienyl | -CH(C₆H₅)₂ | -H | -S-(4-methylthiazol-2-yl) | -CH(C₆H₅)- | -CH₃ |

-continued

Col. VII

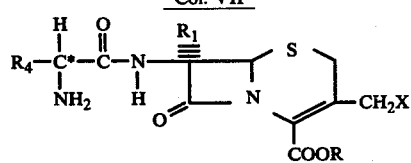

| Ex. | R₄ | R | R₁ | X | A | R₃ |
|---|---|---|---|---|---|---|
| 53 | phenyl | —Si(CH₃)₃ | —H | 2-(1-ethylidene)-1,3,4-thiadiazol-5-ylthio | —CH₂— | —H |
| 54 | 2-furyl | —CH₂CCl₃ | —OCH₃ | 1,3,4-thiadiazol-2-ylthio | —CH₂— | —CH₃ |
| 55 | 4-hydroxyphenyl | -t-C₄H₉ | —H | 1,3,4-thiadiazol-2-ylthio | —CH(C₂H₅)— | —H |
| 56 | 2-thienyl | —CH₂— phenyl | —OCH₃ | 4-methylthiazol-2-ylthio | —CH₂— | —CH₃ |
| 57 | 2-furyl | —CH₂— phenyl | —H | 4-methylthiazol-2-ylthio | —(CH₂)₂— | —H |
| 58 | phenyl | -t-C₄H₉ | —H | 4-methylthiazol-2-ylthio | —CH(phenyl)— | —H |
| 59 | 4-hydroxyphenyl | —CH₂CCl₃ | —OCH₃ | 5-methyl-1,3,4-oxadiazol-2-ylthio | —CH₂— | —H |
| 60 | 2-thienyl | —CH(phenyl)₂ | —H | 1-methyl-1,2,3,4-tetrazol-5-ylthio | —CH₂— | —CH₃ |
| 61 | 2-thienyl | —CH(phenyl)₂ | —OCH₃ | 1H-1,2,3,4-tetrazol-5-ylthio | —CH₂— | —H |
| 62 | 2-furyl | —CH₂-phenyl | —H | 1H-1,2,3,4-tetrazol-5-ylthio | —CH₂— | —H |
| 63 | phenyl | —CH₂CCl₃ | —OCH₃ | 1-methyl-1,2,3,4-tetrazol-5-ylthio | —C(CH₃)₂— | —CH₃ |
| 64 | phenyl | -t-C₄H₉ | —H | 1-methyl-1,2,3,4-tetrazol-5-ylthio | —CH₂— | —H |
| 65 | 4-hydroxyphenyl | —CH₂-phenyl | —OCH₃ | 1-methyl-1,2,3,4-tetrazol-5-ylthio | —CH₂— | —H |
| 66 | 2-thienyl | —Si(CH₃)₃ | —H | —O—C(=O)—CH₃ | —CH₂— | —H |

-continued

Col. VII

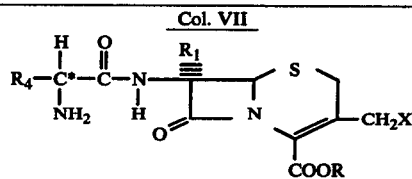

| Ex. | R4 | R | R1 | X | A | R3 |
|---|---|---|---|---|---|---|
| 67 | (2-thienyl) | —CH2—O—C(O)—CH3 | —OCH3 | -S-(1-methyltetrazol-5-yl) | —CH2— | —CH3 |
| 68 | (phenyl) | —CH(CH3)—O—C(O)—C(CH3)3 | —H | -S-(1-methyltetrazol-5-yl) | —CH2— | —H |
| 69 | (phenyl) | —CH2—(phenyl) | —H | —H | —CH2— | —H |
| 70 | (2-thienyl) | —CH2—(phenyl) | —H | —H | —CH2— | —CH3 |

The α-amino cephalosporanic acid compound of either Col. I or Col. VII may be in either the D- or L-form or may be a mixture of D- and L-isomers.

EXAMPLES 71–90

Following the procedure of examples 13 and 14 but employing the acylating agent shown in Col. I (the carboxyl group can be converted into an activated form as shown in examples 13 and 14) and the 7β-amino cephalosporanic acid ester shown in Col. II one obtains the compound shown in Col. III.

| Ex. | R4 | R3 | A | R1 | R | X |
|---|---|---|---|---|---|---|
| 71 | (2-thienyl) | —H | —CH2— | —H | —Si(CH3)3 | -S-(5-methyl-1,3,4-thiadiazol-2-yl) |
| 72 | (2-thienyl) | —CH3 | ⟨CH2⟩2 | —OCH3 | —CH(phenyl)2 | -S-(5-methyl-1,3,4-oxadiazol-2-yl) |
| 73 | (5-methyl-2-thienyl) | —H | —CH(CH3)— | —H | —CH2—(phenyl) | -S-(1-methyltetrazol-5-yl) |
| 74 | (2-furyl) | —C2H5 | ⟨CH2⟩4 | —H | -t-C4H9 | -S-(1-methyltetrazol-5-yl) |

-continued

| | Col. I | | | Col. II | | | Col. III | |
|---|---|---|---|---|---|---|---|---|
| Ex. | R₄ | R₃ | A | R₁ | R | X |

| Ex. | R₄ | R₃ | A | R₁ | R | X |
|---|---|---|---|---|---|---|
| 75 | 5-chloro-2-furyl | —H | —C(CH₃)₂— | —OCH₃ | —CH₂CCl₃ | -S-(1H-1,2,3-triazol-4-yl) |
| 76 | 2-furyl | -n-C₃H₇ | —CH₂— | —H | -t-C₄H₉ | -S-(5-ethyl-1,3,4-thiadiazol-2-yl) |
| 77 | 2-pyridyl | —H | —(CH₂)₆— | —H | —CH(C₆H₅)₂ | -S-(1,3,4-thiadiazol-2-yl) |
| 78 | 2-pyridyl | —CH₃ | —CH(CH₃)— | —OCH₃ | —CH(C₆H₅)₂ | -S-(4-methylisothiazol-5-yl) |
| 79 | phenyl | —H | —CH₂— | —H | —Si(CH₃)₃ | -S-(1-methyltetrazol-5-yl) |
| 80 | phenyl | —CH₃ | —C(CH₃)₂— | —OCH₃ | —Si(CH₃)₃ | -S-(1-methyltetrazol-5-yl) |
| 81 | 4-hydroxyphenyl | —H | —CH₂— | —H | —CH(C₆H₅)₂ | -S-(3-methylisoxazol-5-yl) |
| 82 | 4-hydroxyphenyl | —CH₃ | —CH₂— | —OCH₃ | —CH(C₆H₅)₂ | -S-(1-methyltetrazol-5-yl) |
| 83 | benzyl | —H | —(CH₂)₄— | —H | —CH₂C₆H₅ | -S-(1-methyltetrazol-5-yl) |
| 84 | 4-chlorobenzyl | —H | —CH₂— | —OCH₃ | —CH₂C₆H₅ | -S-(5-methyl-1,3,4-thiadiazol-2-yl) |
| 85 | 1,4-cyclohexadienyl | —CH₃ | —CH₂— | —H | —CH₂C₆H₅ | -S-(1-methyl-4,5-dihydro-1,2,3-triazol-5-yl) |

-continued

| | Col. I | Col. II | Col. III | | | |
|---|---|---|---|---|---|---|
| | R₄—CH—C—OH with NH, C=O, N—A—CN, R₃ (O double bond on C) | H₂N with R₁, S, N, CH₂X, COOR (β-lactam) | R₄—CH—C—N—(β-lactam with R₁, S, CH₂X, COOR), NH, C=O, N—A—CN, R₃ | | | |

| Ex. | R₄ | R₃ | A | R₁ | R | X |
|---|---|---|---|---|---|---|
| 86 | phenyl | —C₂H₅ | —CH₂— | —H | —CH(C₆H₅)₂ | —O—C(=O)—CH₃ |
| 87 | thienyl (S) | —H | —CH₂— | —H | —CH(C₆H₅)₂ | —H |
| 88 | thienyl (S) | —H | —CH(C₆H₅)— | —H | —CH(C₆H₅)₂ | —S-(1-methyltetrazol-5-yl) |
| 89 | phenyl | —H | —CH(C₆H₅)— | —H | —CH₂(C₆H₅)₂ | —S-(5-methyl-1,3,4-thiadiazol-2-yl) |
| 90 | thienyl (S) | —CH₃ | —CH(2-thienyl)— | —OCH₃ | —Si(CH₃)₃ | —S-(1-methyltetrazol-5-yl) |

The acylating agent of Col. I may be in either the D- or L-form or may be a mixture of D- and L-isomers.

The resulting esters of Col. III can be treated according to known methods to remove the ester protecting group and yield the corresponding final product wherein R is hydrogen.

EXAMPLE 91

7β-[[D-[[[(Cyanomethyl)amino]carbonyl]amino]-phenylacetyl]amino]-3-[[4-(aminocarbonyl)pyridino]-methyl]-8-oxo-5-thia-1-azabicyclo[4.2.0]oct-2-ene-2-carboxylic acid (a)
3-[(Acetyloxy)methyl]-7β-[[D-[[[(cyanomethyl)amino]-carbonyl]amino]phenylacetyl]amino]-8-oxo-5-thia-1-azabicyclo[4.2.0]oct-2-ene-2-carboxylic acid, sodium salt 4.87 g. (0.01 mole) of 7β-D-(2-amino-2-phenylacetamido-3-[(acetyloxy)methyl]-8-oxo-5-thia-1-azabicyclo[4.2.0]oct-2-ene-2-carboxylic acid, trifluoroacetic acid salt are brought into solution at room temperature in 40 ml. of methylene chloride by the addition of 2.64 ml. of triethylamine. A solution of 1.23 g. of isocyanatomethylnitrile in 40 ml. of methylene chloride is added dropwise. The mixture is stirred for one hour, concentrated, the viscous residue is taken up in water, washed twice with ether and acidified 2N hydrochloric acid to precipitate 4.8 g. of 3-[(acetyloxy)methyl]-7β-[[D-[[[(cyanomethyl)amino]carbonyl]amino]-phenylacetyl]amino]-8-oxo-5-thia-1-azabicyclo[4.2.0]oct-2-ene-2-carboxylic acid.

This acid is brought into solution in 75 ml. of absolute methanol by the addition of triethylamine. The solution is filtered and sodium ethyl hexanoate in methanol/ether (1:1) is added to the filtrate. After a short period of time 2.1 g. of 3-[(acetyloxy)methyl]-7β-[[D-[[[(cyanomethyl)amino]carbonyl]amino]phenylacetyl-]amino]-8-oxo-5-thia-1-azabicyclo[4.2.0]oct-2-ene-2-carboxylic acid, sodium salt crystallize. By the addition of ether to the mother liquor an additional 1.3 g. of sodium salt are obtained.

(b)
7β-[[D-[[[(Cyanomethyl)amino]carbonyl]amino]-phenylacetyl]-amino]-3-[[4-(aminocarbonyl)pyridino]-methyl]-8-oxo-5-thia-1-azabicyclo[4.2.0]oct-2-ene-2-carboxylic acid A mixture of 1.9 g. of the sodium salt from part (a), 9 g. of potassium thiocyanate, 0.69 g. of isonicotinamide, and 6 ml. of water is heated at 50° overnight. The resulting reaction mixture is purified on an ion exchange column containing 70 g. of Amberlite XAD-2. The titled compound is eluted from the column with a mixture of methanol:water (20:80). After evaporating the methanol, the aqueous solution is lyophilized to yield 1.2 g. of crude product. This material is treated with 20 ml. of ethanol and filtered under suction to yield 0.85 g. of 7β-[[D-[[[(cyanomethyl)amino]carbonyl]-amino]-phenylacetyl]amino]-8-oxo-5-thia-1-azabicyclo[4.2.0]oct-2-ene-2-carboxylic acid; m.p.170° (dec.).

EXAMPLE 92

7β-[[D-[[[(Cyanomethyl)amino]carbonyl]amino]-2-thienylacetyl]amino]-3-[[4-(aminocarbonyl)pyridino]-methyl]-8-oxo-5-thia-1-azabicyclo[4.2.0]oct-2-ene-2-carboxylic acid (a)

3-[(Acetyloxy)methyl-7β-[[D-[[[(4-methoxyphenyl)methoxy]-carbonyl]amino]-2-thienylacetyl]amino]-8-oxo-5-thia-1-azabicyclo[4.2.0]oct-2-ene-2-carboxylic acid 3.2 g. (0.01 mole) of the D-2-[[[(4-methoxyphenyl)-methoxy]carbonyl]amino]-2-thiopheneacetic acid from example 1(a) are brought into solution in 40 ml. of methylene chloride with 1.1 ml. of N-methylmorpholine. The solution is cooled to −15°, 1.39 ml. of isobutylchloroformate are added, and the mixture is stirred for 10 minutes. To this is added a solution of 3.26 g. (0.1012 mol.) of 7-aminocephalosporanic acid and 3.1 ml. of triethylamine in 40 ml. of methylene chloride. The mixture is stirred for 1 hour at −5° and 1 hour at 5°. This mixture is then evaporated to dryness in a rotary evaporator. The solid residue is triturated with ether and filtered under suction. The substance is then dissolved in ice water, layered over with ethyl acetate and acidified to pH 2.5. The layers are separated, the aqueous layer is extracted once more with ethyl acetate, the combined ethyl acetate extracts are washed with water, dried with magnesium sulfate and concentrated. The residue (4.9 g.) is dissolved in 200 ml. of ethyl acetate and the solution is treated with activated carbon. After filtration, 2 g. of 3-[(acetyloxy)methyl]-7β-[[D-[[[(4-methoxyphenyl)methoxy]carbonyl]amino]-2-thienylacetyl]amino]-8-oxo-5-thia-1-azabicyclo[4.2.0]oct-2-ene-2-carboxylic acid, crystallize; m.p. 142°–143° (dec.).

(b)

3-[(Acetyloxy)methyl]-7β[D-2-amino-2-(2-thienyl)-acetamido]-8-oxo-5-thia-1-azabicyclo[4.2.0]oct-2-ene-2-carboxylic acid, trifluoroacetic acid salt (1:1)

2.0 g. of the product from part (a) are added at −5° to a mixture of 10 ml. of trifluoroacetic acid and 4 ml. of anisole. The mixture is stirred for 10 minutes and is then concentrated in a rotary evaporator. The residue is treated with ether and filtered to yield the titled compound.

(c)

3-[(Acetyloxy)methyl]-7β-[[D-[[[(cyanomethyl)amino]-carbonyl]-amino]-2-thienylacetyl]amino]-8-oxo-5-thia-1-azabicyclo[4.2.0]oct-2-ene-2-carboxylic acid, sodium salt The trifluoroacetic acid salt product from part (b) is treated with isocyanatoacetonitrile according to the procedure of example 1(f) to yield 3-[(acetyloxy)methyl]-7β-[[D-[[[(cyanomethyl)amino]carbonyl]amino]-2-thienylacetyl]amino]-8-oxo-5-thia-1-azabicyclo[4.2.0]oct-2-ene-2-carboxylic acid.

An equimolar aqueous solution of this compound and sodium bicarbonate is lyophilized to yield 3-[(acetyloxy)-methyl]-7β-[[D-[[[(cyanomethyl)amino]carbonyl]amino]-2-thienylacetyl]amino]-8-oxo-5-thia-1-azabicyclo[4.2.0]oct-2-ene-2-carboxylic acid, sodium salt as a powder.

(d)

7β-[[D-[[[(Cyanomethyl)amino]carbonyl]amino]-2-thienylacetyl]amino]-3-[[4-(aminocarbonyl)pyridino]-methyl]-8-oxo-5-thia-1-azabicyclo[4.2.0]oct-2-ene-2-carboxylic acid A mixture of 0.0005 mole of the sodium salt product of part (c), 0.0075 mole of 4-pyridinecarboxamide, 12 g. of potassium thiocyanate, and 7.5 ml. of water are heated at 50° for 24 hours. The clear solution is passed through a chromatography column filled with 150 g. of ion exchanger Amberlite XAD-2. The column is washed with about 3 liters of water and the titled compound is eluted with a mixture of water:methanol (8:2). The methanol is evaporated from the eluate and the aqueous solution is lyophilized. The amorphous residue is triturated with ether and filtered under suction to yield 0.7 g. of 7β-[[D-[[[(cyanomethyl)-amino]carbonyl]amino]-2-thienylacetyl]amino]-3-[[4-aminocarbonyl)pyridino]methyl]-8-oxo-5-thia-1-azabicyclo[4.2.0]-oct-2-ene-2-carboxylic acid.

Similarly, by employing the L-2-[[[(4-methoxyphenyl)-methoxy]carbonyl]amino]-2-thiopheneacetic acid from example 2(a) in place of the D-isomer in the above procedure, one obtains 7β-[[L-[[[(cyanomethyl-)amino]carbonyl]amino]-2-thienylacetyl]amino]-3-[[4-(aminocarbonyl)pyridino]methyl]-8-oxo-5-thia-1-azabicyclo[4.2.0]oct-2-ene-2-carboxylic acid.

EXAMPLE 93

7α-Methoxy-7β-[[D,L-[[[(cyanomethyl)amino]carbonyl]amino]-2-thienylacetyl]amino]-3-[[4-(aminocarbonyl)pyridino]methyl]-8-oxo-5-thia-1-azabicyclo[4.2.0]oct-2-ene-2-carboxylic acid (a)

3-[(Acetyloxy)methyl]-7α-methoxy-7β-[[D,L-[[[(4-methoxyphenyl)methoxy]carbonyl]amino]-2-thienylacetyl]amino]-8-oxo-5-thia-1-azabicyclo[4.2.0]oct-2-ene-2-carboxylic acid, diphenylmethyl ester D,L-2-[[[(4-Methoxyphenyl)methoxy]carbonyl]amino]-2-thiopheneacetic acid and 3-[(acetyloxy)methyl]-7α-methoxy-7β-amino-8-oxo-5-thia-1-azabicyclo[4.2.0]oct-2-ene-2-carboxylic acid, diphenylmethyl ester are reacted according to either of the procedures set forth in example 10(a) to yield the titled compound.

(b)

3-[(Acetyloxy)methyl]-7α-methoxy-7β-[D,L-2-amino-2-(2-thienyl)acetamido]-8-oxo-5-thia-1-azabicyclo[4.2.0]-oct-2-ene-2-carboxylic acid, trifluoroacetic acid salt (1:1)

The diphenylmethyl ester product from part (a) is reacted with trifluoroacetic acid in the presence of anisole according to the procedure of example 1(e) to yield the titled compound.

(c)

3-[(Acetyloxy)methyl]-7α-methoxy-7β-[[D,L-[[[(cyanomethyl)-amino]carbonyl]amino]-2-thienylacetyl]amino]-8-oxo-5-thia-1-azabicyclo[4.2.0]-oct-2-ene-2-carboxylic acid, sodiuim salt The trifluoroacetic acid salt product from part (b) is treated with isocyanatoacetonitrile according to the procedure of example 1(f) to yield 3-[(acetyloxy)methyl]-7α-methoxy-7β-[[D,L-[[[(cyanomethyl)amino]carbonyl]amino]-2-thienylacetyl]amino]-8-oxo-5-thia-1-azabicyclo[4.2.0]oct-2-ene-2-carboxylic acid.

An equimolar solution of this compound and sodium bicarbonate is lyophilized to yield 3-[(acetyloxy)methyl]-7α-methoxy-7β-[[D,L-[[[(cyanomethyl)amino]carbonyl]amino]-2-thienylacetyl]amino]-8-oxo-5-thia-1-azabicyclo[4.2.0]oct-2-ene-2-carboxylic acid, sodium salt as a powder.

(d)

7α-Methoxy-7β-[[D,L-[[[(cyanomethyl)amino]carbonyl]amino]-2-thienylacetyl]amino]-3-[[4-aminocarbonyl]pyridino]methyl]-8-oxo-5-thia-1-azabicyclo[4.2.0]oct-2-ene-2-carboxylic acid An aqueous mixture of the sodium salt product of part (c), 4-pyridinecarboxamide, and potassium thiocyanate is reacted according to the procedure of example 92(d) to yield the titled compound.

EXAMPLE 94

7β-[[D-[[[(Cyanomethyl)methylamino]carbonyl]amino]phenylacetyl]amino]-3-[[4-(aminocarbonyl)pyridino]methyl]-8-oxo-5-thia-1-azabicyclo[4.2.0]oct-2-ene-2-carboxylic acid (a)

3-[(Acetyloxy)methyl]-7β-[[D-[[[(cyanomethyl)methylamino]carbonyl]amino]phenylacetyl]amino]-8-oxo-5-thia-1-azabicyclo[4.2.0]oct-2-ene-2-carboxylic acid, diphenylmethyl ester D-[[[(Cyanomethyl)methylamino]carbonyl]amino]phenylacetic acid from example 14(b) and 3-[(acetyloxy)methyl]-7β-amino-8-oxo-5-thia-1-azabicyclo[4.2.0]oct-2-ene-2-carboxylic acid, diphenylmethyl ester are reacted in the presence of dicyclohexylcarbodiimide according to the procedure of example 1(d) to yield the titled compound.

(b)

3-[(Acetyloxy)methyl]-7β-[[D-[[[(cyanomethyl)methylamino]-carbonyl]amino]phenylacetyl]amino]-8-oxo-5-thia-1-azabicyclo[4.2.0]oct-2-ene-2-carboxylic acid, sodium salt The diphenylmethyl ester from part (a) is treated with trifluoroacetic acid and anisole according to the procedure of example 1(e) to yield 3-[(acetyloxy)methyl]-7β-[[D-[[[(cyanomethyl)methylamino]carbonyl]amino]phenylacetyl]amino]-8-oxo-5-thia-1-azabicyclo[4.2.0]oct-2-ene-2-carboxylic acid.

An equimolar aqueous solution of this compound and sodium bicarbonate is lyophilized to yield 3-[(acetyloxy)methyl]-7β-[[D-[[[(cyanomethyl)methylamino]carbonyl]amino]-phenylacetyl]amino]-8-oxo-5-thia-1-azabicyclo[4.2.0]oct-2-ene-2-carboxylic acid, sodium salt as a powder.

(c)

7β-[[D-[[[(Cyanomethyl)methylamino]carbonyl]amino]-phenylacetyl]amino]-3-[[4-(aminocarbonyl)pyridino]methyl]-8-oxo-5-thia-1-azabicyclo[4.2.0]oct-2-ene-2-carboxylic acid An aqueous mixture of the sodium salt product of part (c), 4-pyridinecarboxamide, and potassium thiocyanate are reacted according to the procedure of example 92(d) to yield the titled compound.

Similarly, by employing L-[[[(cyanomethyl)methylamino]-carbonyl]amino]phenylacetic acid in part (a) of example 94, one obtains 7β-[[L-[[[(cyanomethyl)methylamino]carbonyl]-amino]phenylacetyl]amino]-3-[[4-(aminocarbonyl)pyridino]-methyl]-8-oxo-5-thia-1-azabicyclo[4.2.0]oct-2-ene-2-carboxylic acid. Also, by following the procedure of example 94 but employing 7α-methoxy-7β-amino-3-[(acetyloxy)methyl]-8-oxo-5-thia-1-azabicyclo[4.2.0]oct-2-ene-2-carboxylic acid, diphenylmethyl ester in part (a) for the desmethoxy compound, one obtains 7α-methoxy-7β-[[D-[[[(cyanomethyl)methylamino]carbonyl]-amino]phenylacetyl]amino]-3-[[4-(aminocarbonyl)pyridino]-methyl]-8-oxo-5-thia-1-azabicyclo[4.2.0]oct-2-ene-2-carboxylic acid.

EXAMPLES 95–111

Following the procedures of examples 91 to 94, but employing the cephalosporanic acid sodium salt shown below in Col. I and the pyridine compound shown in Col. II, one obtains the product shown in Col. III.

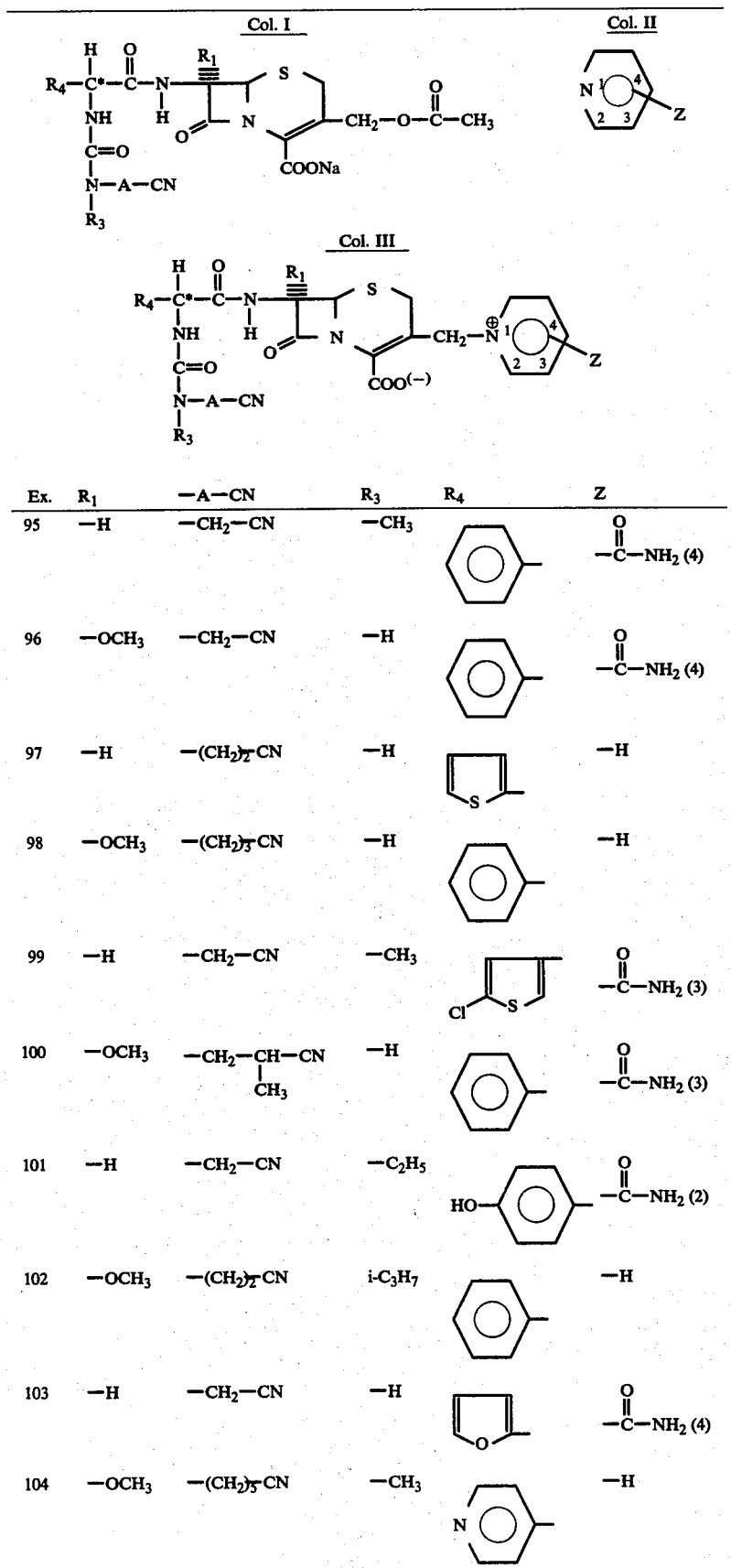

-continued

Col. I: (cephalosporin structure with R1, R4, C*, NH, C=O, N-A-CN, R3, S, N, CH2-O-C(=O)-CH3, COONa)

Col. II: (6-membered ring with N at position 1, Z at position 4)

Col. III: (cephalosporin structure with R1, R4, C*, NH, C=O, N-A-CN, R3, S, N, CH2-N⊕(ring with Z), COO⁻)

| Ex. | R₁ | —A—CN | R₃ | R₄ | Z |
|---|---|---|---|---|---|
| 105 | —H | —CH₂—CN | —H | thienyl | $-\overset{O}{\underset{}{C}}-NH_2$ (4) |
| 106 | —OCH₃ | —(CH₂)₃—CN | —CH₃ | 2,4-dichlorophenyl | —H |
| 107 | —H | —C(CH₃)₂—CN | —H | phenyl | —H |
| 108 | —OCH₃ | —CH(phenyl)—CN | —CH₃ | thienyl | $-\overset{O}{\underset{}{C}}-NH_2$ (4) |
| 109 | —H | —C(C₂H₅)₂—CN | —C₂H₅ | cyclohexenyl | —H |
| 110 | —OCH₃ | —CH₂—CN | —CH₃ | cyclohexenyl | $-\overset{O}{\underset{}{C}}-NH_2$ (4) |
| 111 | —H | —CH(C₃H₇)—CN | —H | phenyl | $-\overset{O}{\underset{}{C}}-NH_2$ (4) |

The cephalosporanic acid sodium salts shown above in Col. I may be in the D- or L-isomer form or a mixture of D- and L- isomers.

EXAMPLE 112

7β-[[D-[[[(Cyanomethyl)amino]carbonyl]amino]-2-thienylacetyl]-amino]-3-[[(1-oxo-2-pyridinyl)thio]methyl]-8-oxo-5-thia-1-azabicyclo[4.2.0]oct-2-ene-2-carboxylic acid 0.003 mole of 3-[(acetyloxy)methyl]-7β-[[D-[[[(cyanomethyl)amino]carbonyl]amino]-2-thienylacetyl]amino]-8-oxo-5-thia-1-azabicyclo[4.2.0]oct-2-ene-2-carboxylic acid, sodium salt from example 92(c) and 0.004 mole of 2-mercaptopyridine, 1-oxide, sodium salt are dissolved in 15 ml. of water and heated overnight at 50°. The reaction mixture is then diluted with water, filtered, and the clear solution is adjusted to a pH of 2 by the addition of 2N hydrochloric acid. The resulting precipitate is filtered under suction to obtain 7β-[[D-[[[(cyanomethyl)amino]carbonyl]amino]-2- thienylacetyl]amino]-3-[[(1-oxo-2-pyridinyl)thio]methyl]-8-oxo-5-thia-1-azabicyclo[4.2.0]oct-2-ene-2-carboxylic acid.

Following the same procedure but employing 3-[(acetyloxy)methyl]-7β-[[L-[[[(cyanomethyl)amino]carbonyl]amino]-2-thienylacetyl]amino]-8-oxo-5-thia-1-azabicyclo[4.2.0]oct-2-ene-2-carboxylic acid, sodium salt, one obtains the corresponding final product in the L- form.

Similarly, the various 3-[(acetyloxy)methyl]-7α-methoxy or desmethoxy-7β-acylureido-cehalosporanic acid sodium salts of examples 91, 93 or 94 or those shown in Col. I of examples 95 to 111 may be employed in the procedure of example 112 to obtain other 3-[[(1-oxo-2-pyridinyl)thio]-methyl]-cephalosporins within the scope of the invention.

EXAMPLE 113

7β-[[D-[[[(Cyanomethyl)amino]carbonyl]amino]-2-thienylacetyl]amino]-3-[[(1-oxopyridazin-3-yl)thio]methyl]-8-oxo-5-thia-1-azabicyclo[4.2.0]oct-2-ene-2-carboxylic acid 3-[(Acetyloxy)methyl]-7β-[[D-[[[(cyanomethyl)amino]carbonyl]amino]-2-thienylacetyl]amino]-8-oxo-5-thia-1-azabicyclo[4.2.0]oct-2-ene-2-carboxylic acid, sodium salt from example 92(c) is dissolved in a mixture of acetone:water (1:1). 1-Oxopyridazine-3-thiol, sodium salt is added under nitrogen and the solution is heated for several hours at 60°. The solution is diluted with 150 ml. of water and acidified to pH 5 by the addition of 2N hydrochloric acid while cooling. A precipitate forms which is filtered under suction to yield 7β-[[D-[[[(cyanomethyl)amino]carbonyl]amino]-2-thienylacetyl]amino]-3-[[(1-oxopyridazin-3-yl)thio]methyl]-8-oxo-5-thia-1-azabicyclo[4.2.0]oct-2-ene-2-carboxylic acid.

Following the same procedure but employing 3-[(acetyloxy)methyl]-7β-[[L-[[[(cyanomethyl)amino]carbonyl]amino]-2-thienylacetyl]amino]-8-oxo-5-thia-1-azabicyclo[4.2.0]oct-2-ene-2-carboxylic acid, sodium salt, one obtains the corresponding final product in the L- form.

EXAMPLES 114–122

Following the procedure of example 113 but substituting for the 1-oxopyridazine-3-thiol of the following:
2-oxopyridazine-3-thiol
6-methyl-1-oxopyridazine-3-thiol
6-methoxy-1-oxopyridazine-3-thiol
6-t-butyl-2-oxopyridazine-3-thiol
6-ethyl-2-oxopyridazine-3-thiol
6-hydroxy-1-oxopyridazine-3-thiol
6-hydroxy-2-oxopyridazine-3-thiol
6-chloro-1-oxopyridazine-3-thiol
6-chloro-2-oxopyridazine-3-thiol
one obtains:
7β-[[D-[[[(cyanomethyl)amino]carbonyl]amino]-2-thienylacetyl]amino]-3-[[(2-oxopyridazin-3-yl)thio]methyl]-8-oxo-5-thia-1-azabicyclo[4.2.0]oct-2-ene-2-carboxylic acid,
7β-[[D-[[[(cyanomethyl)amino]carbonyl]amino]-2-thienylacetyl]amino]-3-[[(6-methyl-1-oxopyridazin-3-yl)thio]-methyl]-8-oxo-5-thia-1-azabicyclo[4.2.0]oct-2-ene-2-carboxylic acid,
7β-[[D-[[[(cyanomethyl)amino]carbonyl]amino]-2-thienylacetyl]amino]-3-[[(6-methoxy-1-oxopyridazin-3-yl)thio]-methyl]-8-oxo-5-thia-1-azabicyclo[4.2.0]oct-2-ene-2-carboxylic acid,
7β-[[D-[[[(cyanomethyl)amino]carbonyl]amino]-2-thienylacetyl]amino]-3-[[(6-t-butyl-2-oxopyridazin-3-yl)thio]-methyl]-8-oxo-5-thia-1-azabicyclo[4.2.0]oct-2-ene-2-carboxylic acid,
7β-[[D-[[[(cyanomethyl)amino]carbonyl]amino]-2-thienylacetyl]amino]-3-[[(6-ethyl-2-oxopyridazin-3-yl)thio]-methyl]-8-oxo-5-thia-1-azabicyclo[4.2.0]oct-2-ene-2-carboyxlic acid,
7β-[[D-[[[(cyanomethylamino]carbonyl]amino]-2-thienyl-acetyl]amino]-3-[[(6-hydroxy-1-oxopyridazin-3-yl)thio]methyl]-8-oxo-5-thia-1-azabicyclo[4.2.0]oct-2-ene-2-carboxylic acid,
7β-[[D-[[[(cyanomethyl)amino]carbonyl]amino]-2-thienyl-acetyl]amino]-3-[[(6-hydroxy-2-oxopyridazin-3-yl)thio]methyl]-8-oxo-5-thia-1-azabicyclo[4.2.0]oct-2-ene-2-carboxylic acid,
7β-[[D-[[[(cyanomethyl)amino]carbonyl]amino]-2-thienyl-acetyl]amino]-3-[[(6chloro-1-oxopyridazin-3-yl)thio]methyl]-8-oxo-5-thia-1-azabicyclo[4.2.0]oct-2-ene-2-carboxylic acid,
and
7β-[[D-[[[(cyanomethyl)amino]carbonyl]amino]-2-thienyl-acetyl]amino]-3-[[(6-chloro-2-oxopyridazin-3-yl)thio]methyl]-8-oxo-5-thia-1-azabicyclo[4.2.0]oct-2-ene-2-carboxylic acid, respectively.

Similarly, by employing 3-[(acetyloxy)methyl]-7β-[[L-[[[(cyanomethyl)amino]carbonyl]amino]-2-thienylacetyl]-amino-8-oxo-5-thia-1-azabicyclo[4.2.0]oct-2-ene-2-carboxylic acid, sodium salt in place of the D-isomer in examples 113 to 122, the corresponding final products in the L-isomer form are obtained. Additionally, the various 3-[(acetyloxy)methyl]-7α-methoxy or desmethoxy-7β-acylureido-cephalosporanic acid sodium salts of example 91, 93 or 94 or those shown in Col. I of examples 95 to 111 may be employed in the procedure of examples 113 to 122 to obtain other compounds within the scope of the invention.

EXAMPLE 123

7α-Methoxy-7β-[[D,L-[[[(cyanomethyl)amino]carbonyl]amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid 3-[(Acetyloxy)methyl]-7α-methoxy-7β-[[D,L-[[[(cyanomethyl)amino]carbonyl]amino]-2-thienylacetyl]amino]-8-oxo-5-thia-1-azabicyclo[4.2.0]oct-2-ene-2-carboxylic acid prepared as set forth in examplee 93(c) is dissolved in a mixture of acetone:water (1:1) with the aid of 5N sodium hydroxide. The pH is adjusted to 7.6–8.0 and 5 mmol. of 1-methyl-1H-tetrazole-5-thiol is added. The pH is maintained at 7.8 by the addition of 5N sodium hydroxide. The reaction mixture is heated at 50° to 60° for several hours. After cooling and distilling off the acetone, the mixture is acidified to pH 2.5 by the addition of 2N hydrochloric acid while cooling with ice. The resulting precipitate is extracted with ethyl acetate to yield 7α-methoxy-7β-[[D,L-[[[(cyanomethyl)amino]-carbonyl]amino]-2-thienylacetyl]amino]-3-[[(1-methyl-1H-tetrazol-5-yl)thio]methyl]-8-oxo-5-thia-1-azabicyclo[4.2.0]-oct-2-ene-2-carboxylic acid.

EXAMPLES 124–142

Following the procedure of example 123 but employing the 3-[(acetyloxy)methyl]-7α-methoxy or desmethoxy-7β-acylureido cephalosporannic acid shown below in Col. I and the heteromercaptan shown below in Col. II, one obtains the 3-heterothio compounds shown in Col. III.

Col. I

[Structure: R$_4$—C*(H)—C(=O)—NH—CH(R$_1$)—[β-lactam with S]—N—C(COOH)=C—CH$_2$—O—C(=O)—CH$_3$; with NH—C(=O)—N(R$_3$)—A—CN substituent on R$_4$ carbon]

Col. II
hetero—S—H

Col. III

[Structure: R$_4$—C*(H)—C(=O)—NH—CH(R$_1$)—[β-lactam with S]—N—C(COOH)=C—CH$_2$—S—hetero; with NH—C(=O)—N(R$_3$)—A—CN substituent on R$_4$ carbon]

| Ex. | R$_1$ | A—CN | R$_3$ | R$_4$ | hetero |
|---|---|---|---|---|---|
| 124 | —H | —CH$_2$—CN | —H | 2-thienyl | 1-methyl-tetrazol-5-yl |
| 125 | —H | —CH$_2$—CN | —CH$_3$ | 2-thienyl | 5-methyl-1,3,4-thiadiazol-2-yl |
| 126 | —OCH$_3$ | —(CH$_2$)$_2$—CN | H | 2-furyl | 5-methyl-1,3,4-thiadiazol-2-yl |
| 127 | —H | —CH(CH$_3$)—CN | —CH$_3$ | 5-chloro-2-furyl | 5-methyl-1,3,4-oxadiazol-2-yl |
| 128 | —H | —CH$_2$—CN | —H | phenyl | 1-methyl-tetrazol-5-yl |
| 129 | —OCH$_3$ | —C(CH$_3$)$_2$—CN | —CH$_3$ | phenyl | 1-methyl-tetrazol-5-yl |
| 130 | —H | —(CH$_2$)$_4$—CN | —H | 4-hydroxyphenyl | 4-methyl-1,3-thiazol-2-yl |
| 131 | —OCH$_3$ | —CH$_2$—CN | —CH$_3$ | 1,4-cyclohexadienyl | 1-methyl-tetrazol-5-yl |
| 132 | —H | —CH(C$_6$H$_5$)—CN | —H | 2-thienyl | 1-methyl-tetrazol-5-yl |

-continued

Col. I

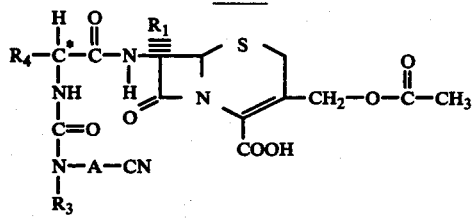

Col. II
hetero—S—H
Col. III

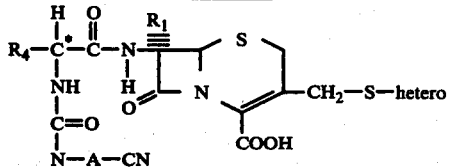

| Ex. | $R_1$ | A—CN | $R_3$ | $R_4$ | hetero |
|---|---|---|---|---|---|
| 133 | —H | $\underset{C_2H_5}{\overset{C_2H_5}{-\underset{|}{\overset{|}{C}}-CN}}$ | —CH$_3$ | 2-thienyl | 1-methyl-tetrazol-5-yl |
| 134 | —OCH$_3$ | $\underset{C_3H_7}{-CH-CN}$ | —C$_2$H$_5$ | cyclohexenyl | 1-methyl-tetrazol-5-yl |
| 135 | —H | —CH$_2$—CN | —H | cyclohexenyl | 2-methyl-1,3,4-thiadiazol-5-yl |
| 136 | —OCH$_3$ | —(CH$_2$)$_2$—CN | $-CH_2-CH\underset{CH_3}{\overset{CH_3}{\big<}}$ | phenyl | 1-methyl-tetrazol-5-yl |
| 137 | —H | —CH$_2$—CN | —C$_2$H$_5$ | phenyl | 1,3,4-thiadiazol-5-yl |
| 138 | —OCH$_3$ | —CH$_2$—CN | —CH$_3$ | —C$_2$H$_5$ | 4-methyl-isothiazol-5-yl / 3-methyl-isoxazol-5-yl |
| 139 | —H | —CH$_2$—CN | —CH$_3$ | 2-pyridyl | 3-methyl-isoxazol-5-yl |
| 140 | —H | —CH$_2$—CN | —H | 2-thienyl | tetrazol-5-yl |
| 141 | —OCH$_3$ | —(CH$_2$)$_2$—CN | —H | benzyl | 1-methyl-tetrazol-5-yl |
| 142 | —OCH$_3$ | $\underset{\text{2-thienyl}}{-CH-CN}$ | —CH$_3$ | phenyl | tetrazol-5-yl |

The 3-[(acetyloxy)methyl]-cephalosporanic acids of Col. I above may be in either the D- or L- isomer form or may be a mixture of the D- and L- isomers.

What is claimed is:

1. A compound of the formula:

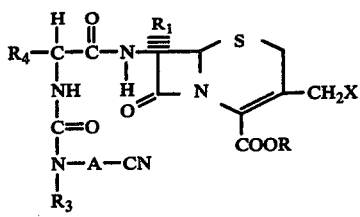

wherein R is hydrogen, straight or branched chain alkyl of 1 to 4 carbons, benzyl, phenethyl, diphenylmethyl, trimethylsilyl, 2,2,2-trichloroethyl, an alkali metal ion, an alkaline earth metal ion, dibenzylamine, N,N-dibenzylethylenediamine, methylamine, triethylamine, N-ethylpiperidine, or

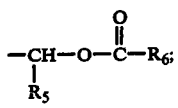

$R_1$ is in the α-configuration and is hydrogen or methoxy; A is straight or branched alkylene of 1 to 8 carbons or

$R_2$ is phenyl, 2-thienyl, or 3-thienyl; $R_3$ is hydrogen or lower alkyl wherein lower alkyl is straight or branched chain of 1 to 8 carbons; $R_4$ is phenyl, benzyl, phenethyl, substituted phenyl, benzyl or phenethyl wherein said substituent is on the phenyl ring and is one or two members selected from the group consisting of chloro, bromo, methyl, ethyl, methoxy, ethoxy and hydroxy, or $R_4$ is a mono-substituted or unsubstituted heterocyclic selected from the group consisting of 2-thienyl, 3-thienyl, 2-furyl, and 3-furyl wherein said heterocyclic substituent is attached at an available carbon atom and is chloro, bromo, methyl, or ethyl; $R_5$ is hydrogen or straight or branched chain alkyl of 1 to 4 carbons; $R_6$ is straight or branched chain alkyl of 1 to 4 carbons; and X is hydrogen

and lower alkyl is straight or branched chain of 1 to 4 carbons,

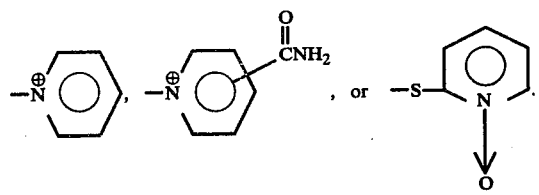

2. The compound of claim 1 wherein R is hydrogen, straight or branched chain alkyl of 1 to 4 carbons, benzyl, phenethyl, diphenylmethyl, sodium, or potassium; A is straight or branched chain alkylene of 1 to 4 carbons

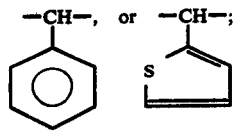

and $R_3$ is hydrogen or straight or branched chain alkyl of 1 to 4 carbons.

3. The compound of claim 2 having the formula:

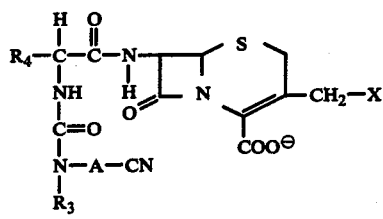

wherein X is

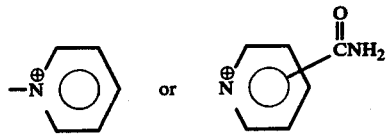

4. The compound of claim 2 wherein X is hydrogen or

and lower alkyl is straight or branched chain of 1 to 4 carbons.

5. The compound of claim 2 wherein X is

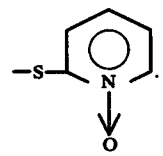

6. The compound of claim 3 wherein X is

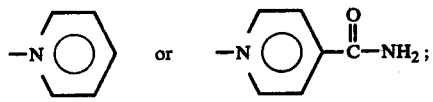

and $R_4$ is 2-thienyl, 3-thienyl, 2-furyl, 3-furyl, phenyl, or p-hydroxyphenyl.

7. The compound of claim 6 wherein X is

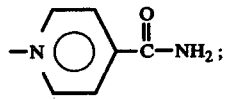

$R_4$ is 2-thienyl; A is $-CH_2-$; and $R_3$ is hydrogen.
8. The compound of claim 6 wherein X is
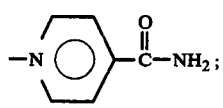
$R_4$ is phenyl; A is $-CH_2-$; and $R_3$ is hydrogen.
9. The compound of claim 4 wherein X is hydrogen or
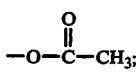
R is hydrogen, sodium or potassium; and $R_4$ is 2-thienyl, 3-thienyl, 2-furyl, 3-furyl, phenyl or 4-hydroxyphenyl.
* * * * *

UNITED STATES PATENT AND TRADEMARK OFFICE
CERTIFICATE OF CORRECTION

PATENT NO. : 4,128,723

DATED : December 5, 1978

INVENTOR(S) : Hermann Breuer et al.

It is certified that error appears in the above-identified patent and that said Letters Patent are hereby corrected as shown below:

Col. 8, line 31, "tetrazole" should read -- tetrazol --.

Col. 9, line 5, -- in vacuo -- should be italicized.

Col. 11, line 64, remove the hyphen between "phenyl" and "acetic"

Col. 11, line 66 & 67, should read -- (4-methoxyphenyl)-methoxy]carbonyl] --. (remove methoxyphenyl)

Col. 12, line 4, should read -- thio]methyl]-8-oxo --.

Col. 13, line 36 should read -- Cyanoethyl)amino]carbonyl] --.

Col. 19, line 33, should read -- 8-oxo --.

Col. 19, line 52 should read -- 7β-[[D,L-[[[D,L-1- --.

Col. 20, line 27 should read -- 7β-D-[[[(cyano --.

Col. 21, line 37, should read --7α-methoxy-7β- --.

UNITED STATES PATENT AND TRADEMARK OFFICE
CERTIFICATE OF CORRECTION

PATENT NO. : 4,128,723

DATED : December 5, 1978

INVENTOR(S) : Hermann Breuer et al.

It is certified that error appears in the above-identified patent and that said Letters Patent are hereby corrected as shown below:

Col. 40, line 38, remove hyphen as follows:--amino]carbonyl--.

Col. 46, line 9, should read -- 7β-[[D-[[[cyanomethyl]amino --.

Col. 46, line 18, should read -- [[6-chloro --

Col. 46, line 49, "examplee" should read -- example --.

Signed and Sealed this

Twentieth Day of March 1979

[SEAL]

Attest:

RUTH C. MASON
Attesting Officer

DONALD W. BANNER
Commissioner of Patents and Trademarks